United States Patent [19]
Douglas et al.

[11] Patent Number: 5,962,215
[45] Date of Patent: Oct. 5, 1999

[54] METHODS FOR TESTING THE CONCENTRATION OF AN ANALYTE IN A BODY FLUID

[75] Inventors: Joel S. Douglas, Santa Clara; Karen R. Drexler; James N. Wilson, both of Los Altos Hills, all of Calif.

[73] Assignee: Mercury Diagnostics, Inc., Scotts Valley, Calif.

[21] Appl. No.: 08/628,489

[22] Filed: Apr. 5, 1996

[51] Int. Cl.$^6$ .................................................. C12Q 1/00
[52] U.S. Cl. ......................... 435/4; 435/13; 435/805; 422/58
[58] Field of Search ............................. 435/4, 14, 25, 435/28, 805, 808, 968, 970, 13; 422/56, 57, 58; 210/617, 631

[56] References Cited

U.S. PATENT DOCUMENTS

| | | | |
|---|---|---|---|
| 3,235,337 | 2/1966 | Artis | 23/253 |
| 3,298,789 | 1/1967 | Mast | 23/253 |
| 3,418,083 | 12/1968 | Rey et al. | 23/253 |
| 3,552,928 | 1/1971 | Fetter | 23/253 |
| 3,607,093 | 9/1971 | Stone | 23/253 |
| 3,630,957 | 12/1971 | Rey et al. | 252/408 |
| 3,723,064 | 3/1973 | Liotta . | |
| 3,964,871 | 6/1976 | Hochstrasser | 23/253 |
| 3,992,158 | 11/1976 | Przybylowicz et al. | 23/253 TP |
| 4,042,329 | 8/1977 | Hochstrasser | 23/230 |
| 4,050,898 | 9/1977 | Goffe et al. | 23/253 |
| 4,059,407 | 11/1977 | Hochstrasser | 23/253 |
| 4,101,381 | 7/1978 | Klose et al. | 195/99 |
| 4,144,306 | 3/1979 | Figueras | 422/56 |
| 4,454,094 | 6/1984 | Bjorling et al. | 422/56 |
| 4,477,575 | 10/1984 | Vogel et al. | 436/170 |
| 4,627,445 | 12/1986 | Garcia et al. | 128/770 |
| 4,637,403 | 1/1987 | Garcia et al. | 128/770 |
| 4,654,310 | 3/1987 | Ly | 436/164 |
| 4,678,757 | 7/1987 | Rapkin et al. . | |
| 4,734,360 | 3/1988 | Phillips | 435/25 |
| 4,738,823 | 4/1988 | Englemann | 422/56 |
| 4,774,192 | 9/1988 | Terminiello et al. | 436/530 |
| 4,787,398 | 11/1988 | Garcia et al. | 128/770 |
| 4,790,979 | 12/1988 | Terminiello et al. | 422/56 |
| 4,810,470 | 3/1989 | Burkhardt et al. | 422/56 |
| 4,824,639 | 4/1989 | Hildenbrand et al. | 422/56 |
| 4,883,764 | 11/1989 | Kloepfer | 436/63 |
| 4,900,666 | 2/1990 | Phillips | 435/25 |
| 4,935,346 | 6/1990 | Phillips et al. | 435/14 |
| 4,994,238 | 2/1991 | Daffern et al. | 422/56 |
| 5,036,000 | 7/1991 | Palmer et al. | 435/26 |
| 5,049,487 | 9/1991 | Phillips et al. | 435/4 |
| 5,059,394 | 10/1991 | Phillips et al. | 422/68 |
| 5,087,556 | 2/1992 | Ertinghausen | 435/7.9 |
| 5,104,619 | 4/1992 | de Castro et al. | 422/56 |
| 5,179,005 | 1/1993 | Phillips et al. | 435/14 |
| 5,186,843 | 2/1993 | Baumgardener et al. | 210/767 |
| 5,187,100 | 2/1993 | Matzinger et al. | 436/16 |
| 5,208,163 | 5/1993 | Charlton et al. | 436/63 |
| 5,211,914 | 5/1993 | Vogel et al. | 422/56 |
| 5,215,886 | 6/1993 | Patel et al. . | |
| 5,231,993 | 8/1993 | Haber et al. | 128/770 |
| 5,271,895 | 12/1993 | McCroskey et al. | 422/58 |
| 5,279,294 | 1/1994 | Anderson et al. | 128/633 |
| 5,290,515 | 3/1994 | Plesch et al. | 422/57 |
| 5,296,194 | 3/1994 | Igarashi | 422/82.05 |
| 5,304,468 | 4/1994 | Phillips et al. | 435/14 |
| 5,306,623 | 4/1994 | Kiser et al. | 435/14 |
| 5,330,715 | 7/1994 | Blake et al. . | |
| 5,413,690 | 5/1995 | Kost et al. | 204/403 |
| 5,413,761 | 5/1995 | Dulaney | 422/56 |
| 5,418,142 | 5/1995 | Kiser et al. | 435/14 |
| 5,426,032 | 6/1995 | Phillips et al. | 435/14 |
| 5,451,350 | 9/1995 | Macho et al. | 264/442 |
| 5,453,360 | 9/1995 | Yu | 435/28 |
| 5,456,835 | 10/1995 | Castino et al. | 210/645 |
| 5,470,533 | 11/1995 | Shindo et al. | 422/63 |
| 5,478,752 | 12/1995 | Lerch et al. | 436/169 |
| 5,504,013 | 4/1996 | Senior . | |
| 5,515,170 | 5/1996 | Matzinger et al. | 356/423 |
| 5,526,120 | 6/1996 | Jina et al. | 356/446 |
| 5,556,761 | 9/1996 | Phillips | 435/14 |
| 5,558,834 | 9/1996 | Chu et al. | 422/55 |
| 5,563,031 | 10/1996 | Yu | 435/4 |
| 5,563,042 | 10/1996 | Phillips et al. | 435/14 |
| 5,582,184 | 12/1996 | Erickson et al. | 128/760 |
| 5,607,565 | 3/1997 | Azarnia et al. | 204/403 |

FOREIGN PATENT DOCUMENTS

| | | |
|---|---|---|
| 0100173 | 6/1984 | European Pat. Off. . |
| 0473241 | 7/1987 | European Pat. Off. . |
| 0479394 | 8/1987 | European Pat. Off. . |
| 0656423 | 8/1987 | European Pat. Off. . |
| 0473241 | 4/1992 | European Pat. Off. . |
| 0574134 | 12/1993 | European Pat. Off. . |
| 0735369 | 3/1995 | European Pat. Off. . |
| WO8501747 | 4/1985 | WIPO . |
| WO92/17768 | 10/1992 | WIPO . |
| WO9607907 | 3/1996 | WIPO . |
| WO9607908 | 3/1996 | WIPO . |

*Primary Examiner*—Ralph Gitomer
*Attorney, Agent, or Firm*—Burns, Doane, Swecker & Mathis, LLP

[57] ABSTRACT

Devices and methods for utilizing dry chemistry dye indicator systems for body fluid analysis such as glucose level in whole blood are provided by incorporating a porous membrane with a skin side which enables separation of whole blood and visually reading the indicator without removing the red blood cell portion of the blood from the membrane. The devices also enable visual reading of the indicator by use of a cellulose fiber glass composite matrix which provides separation of whole blood in a lateral flow of the blood through the matrix from the input area to a test area of the matrix. Another aspect of the device provides a determination of hematocrit level in whole blood by measuring flow rate through a restricted passageway in the device.

6 Claims, 21 Drawing Sheets

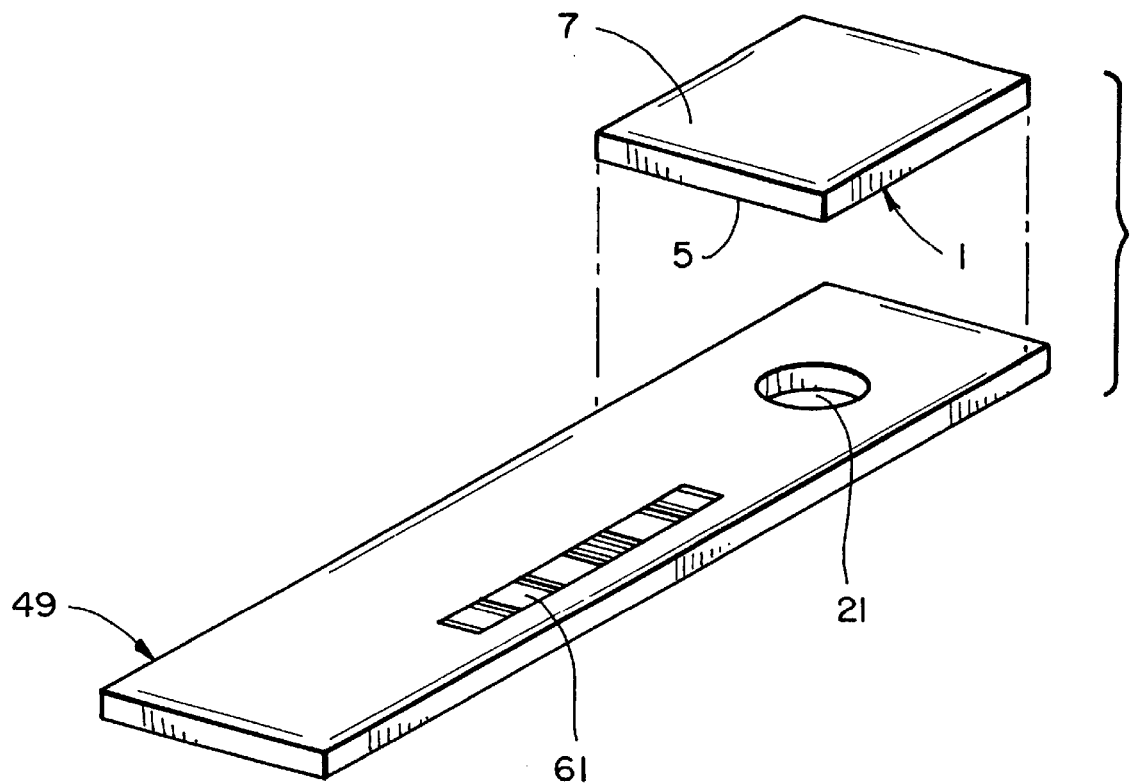
FIG_1
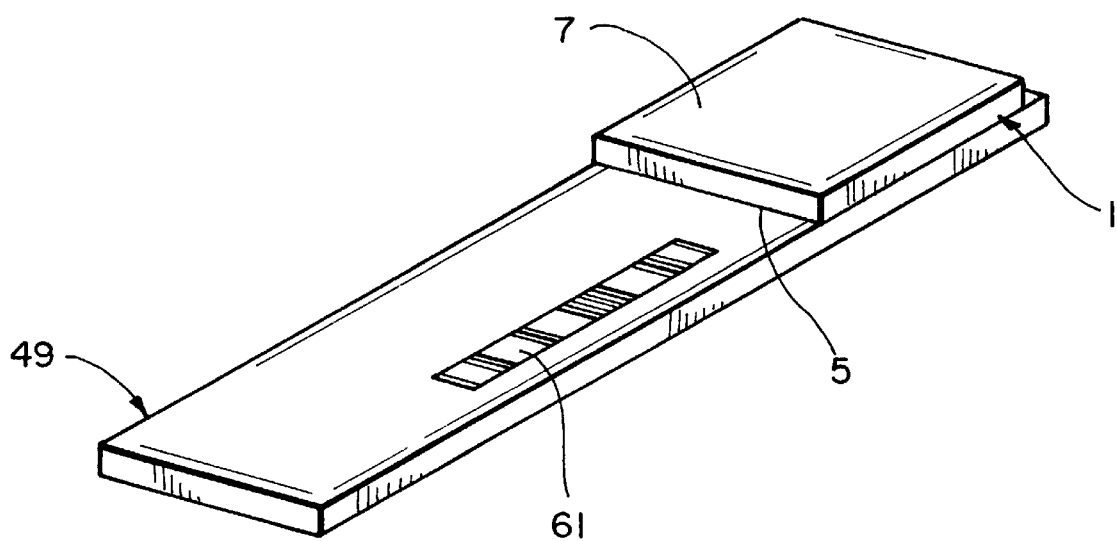
FIG_2

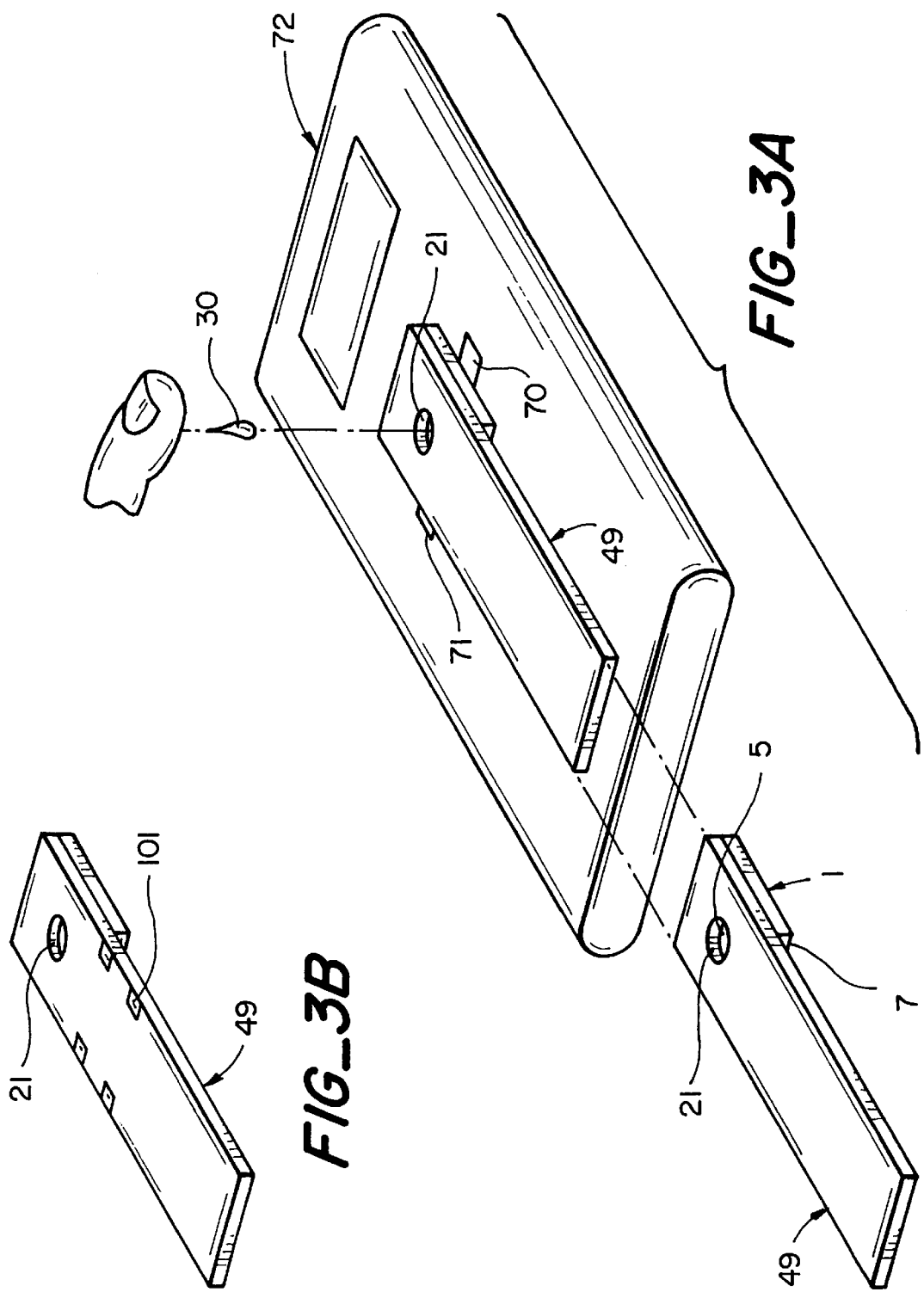

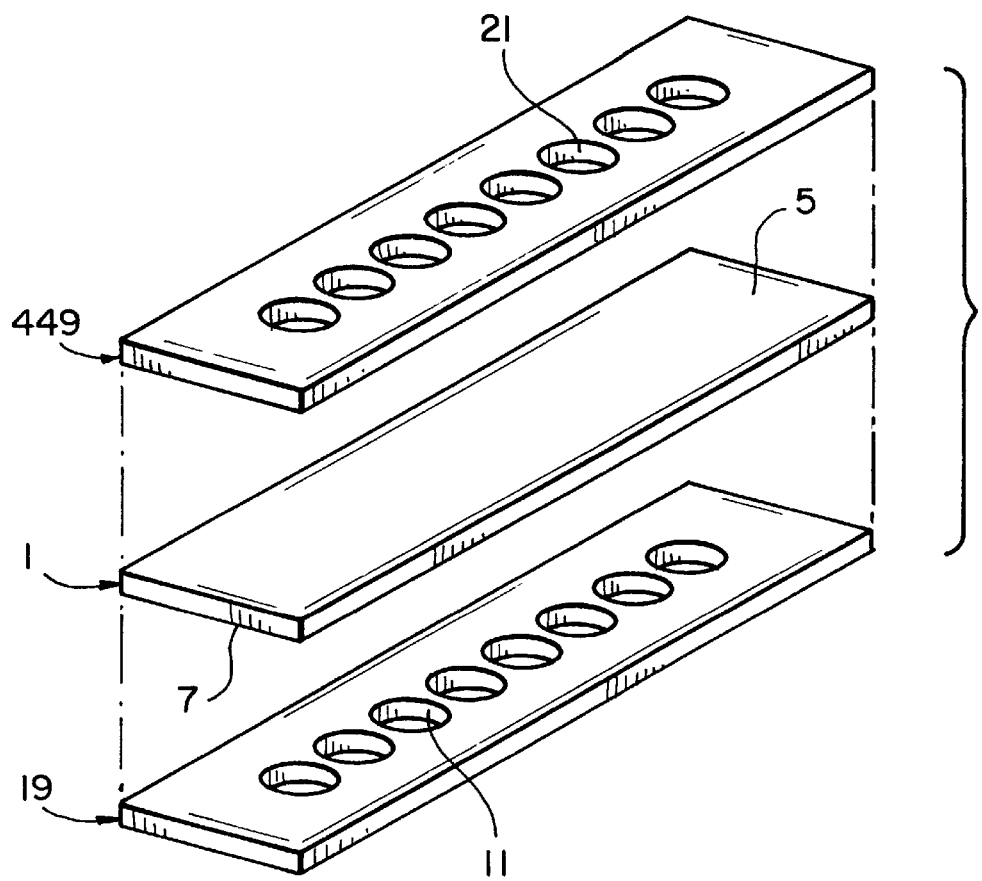
FIG_4
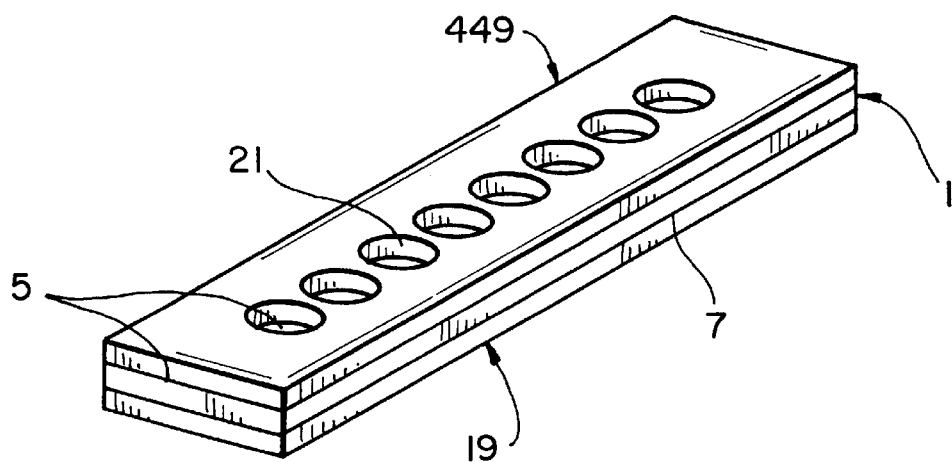
FIG_5

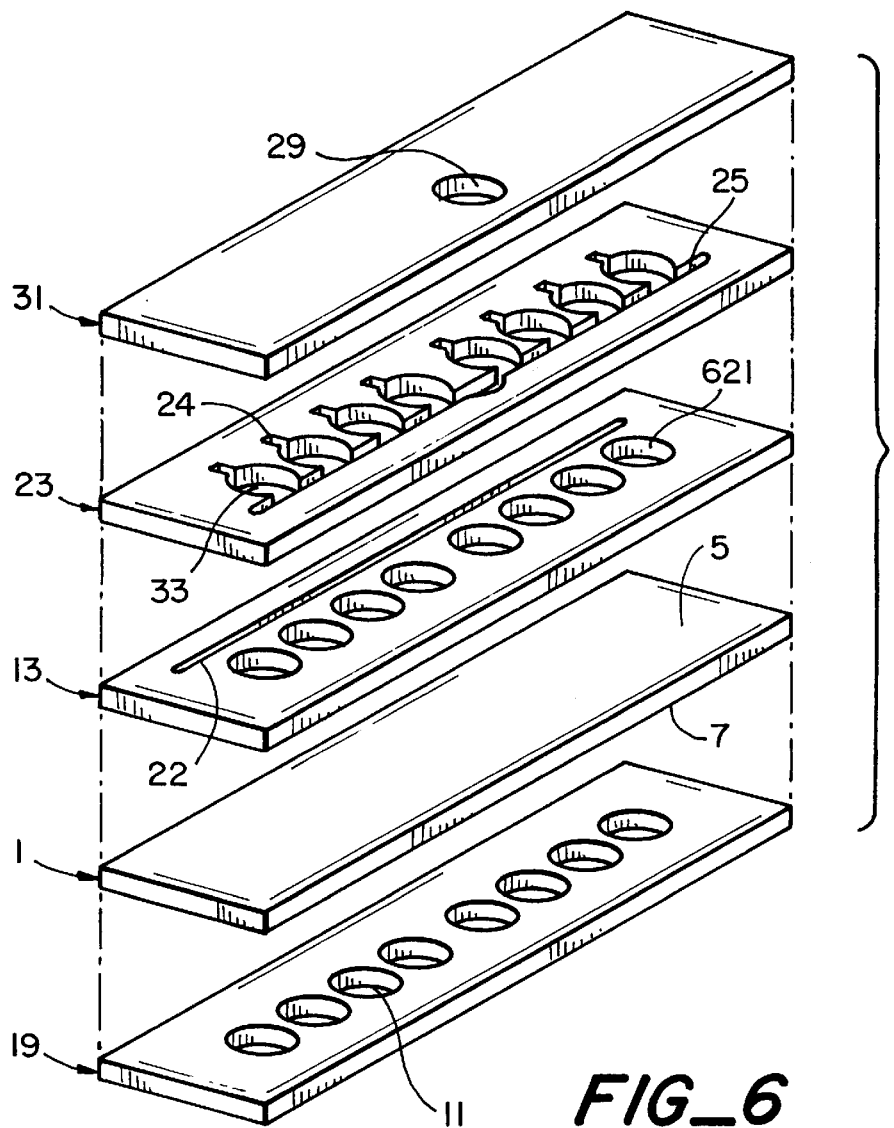
FIG_6
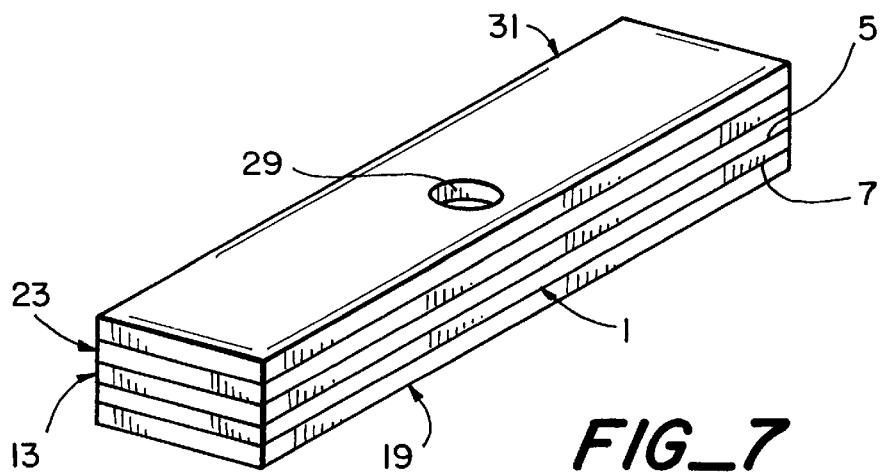
FIG_7

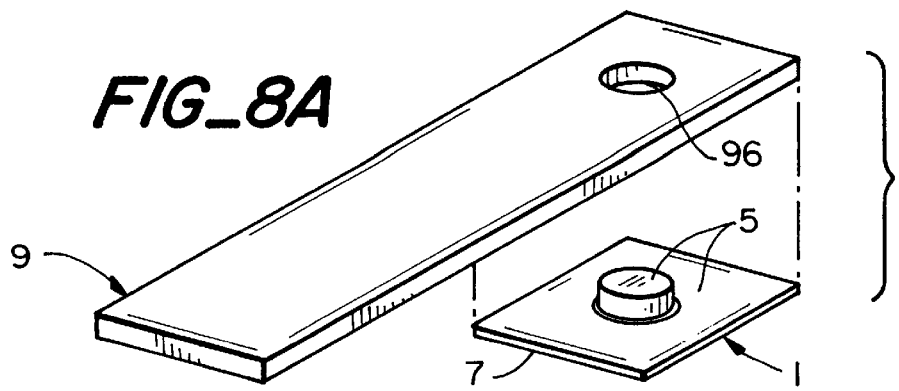
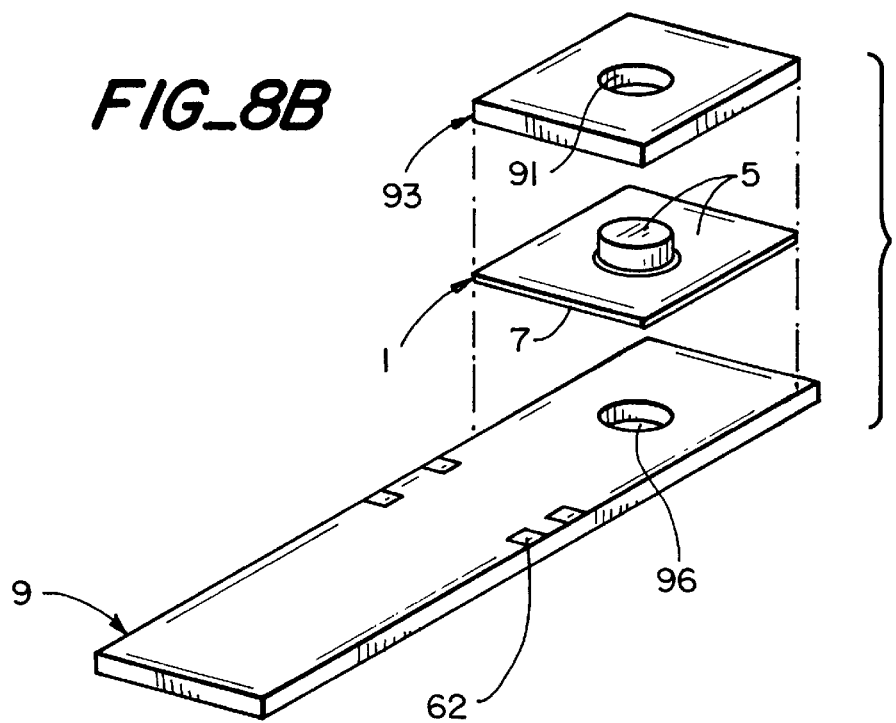
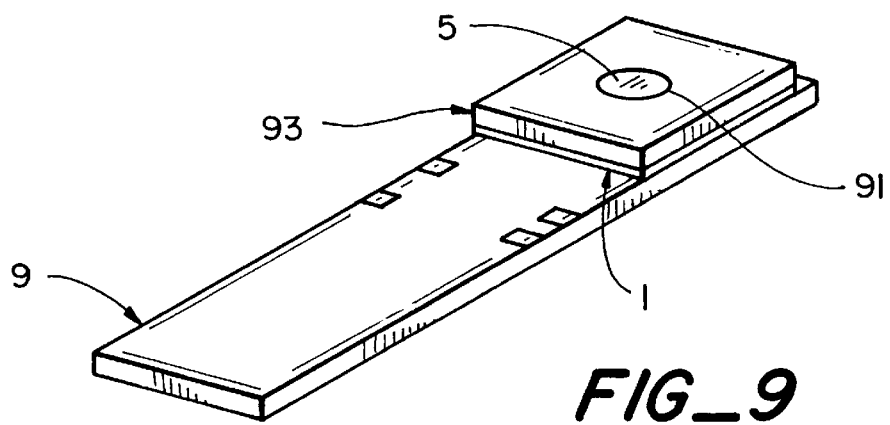

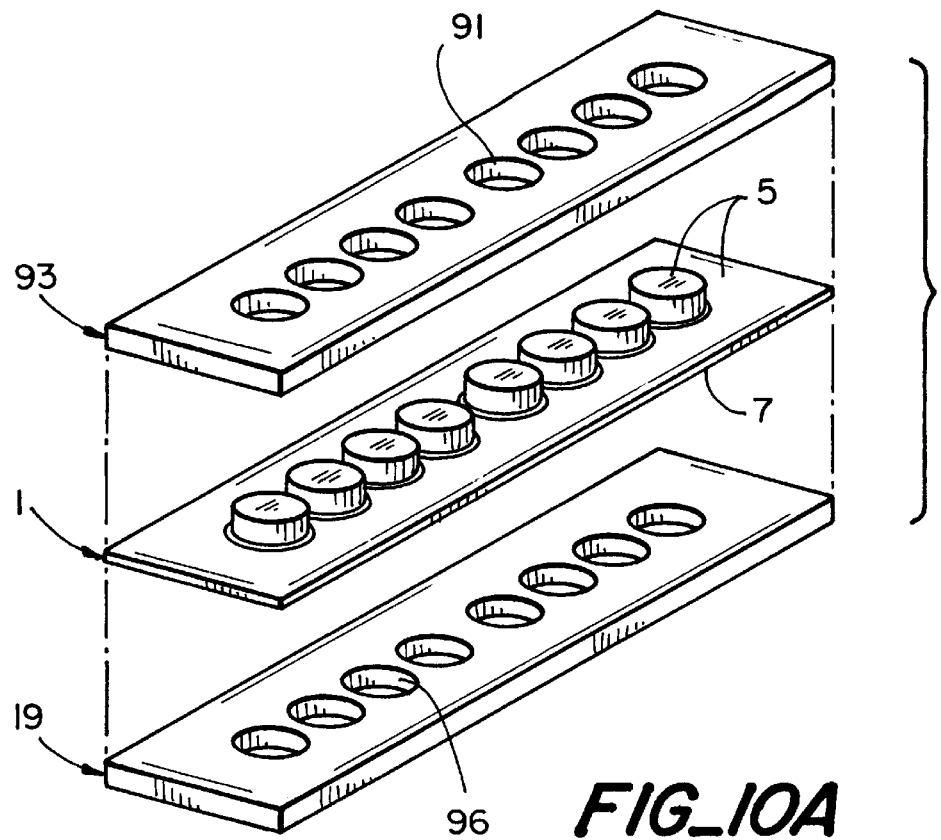
FIG_10A
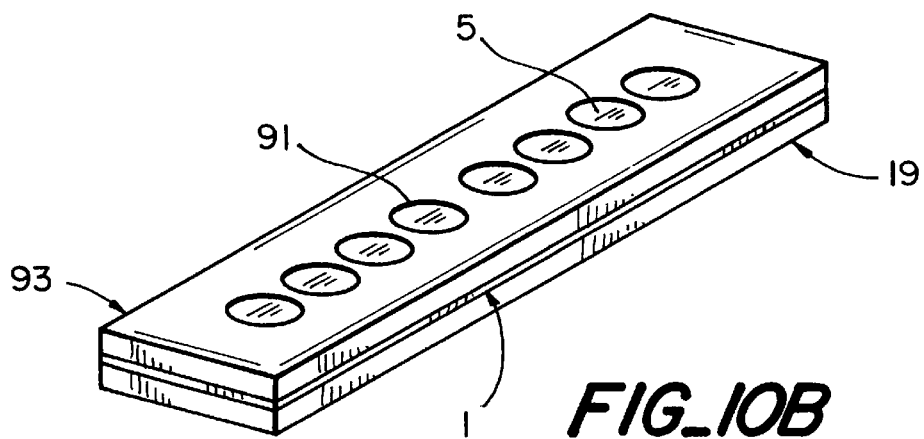
FIG_10B
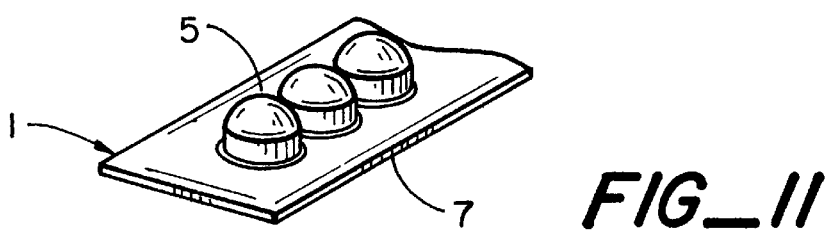
FIG_11

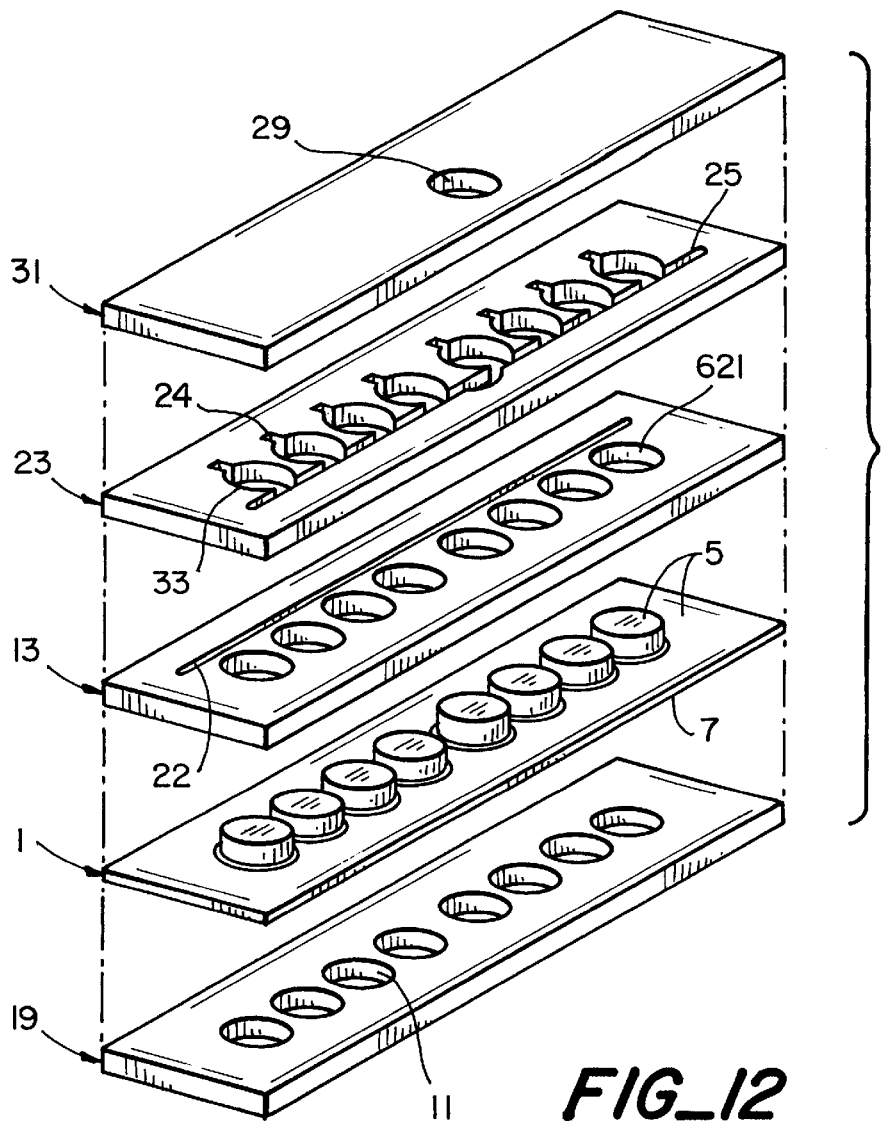
FIG_12
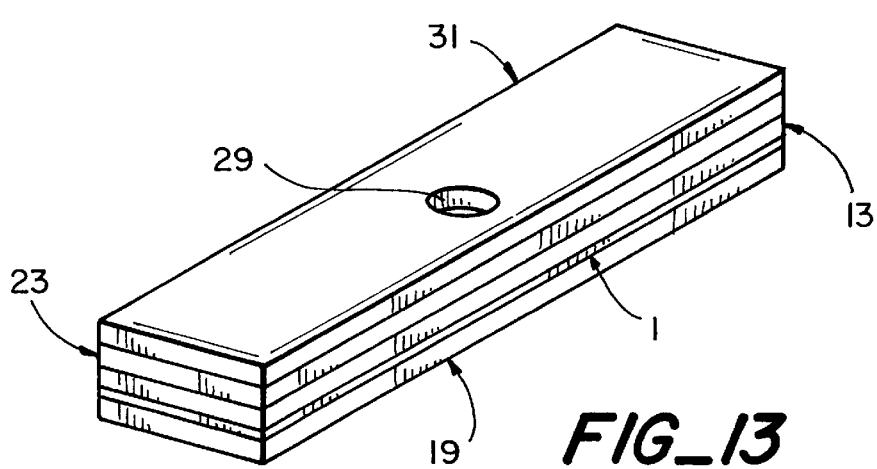
FIG_13

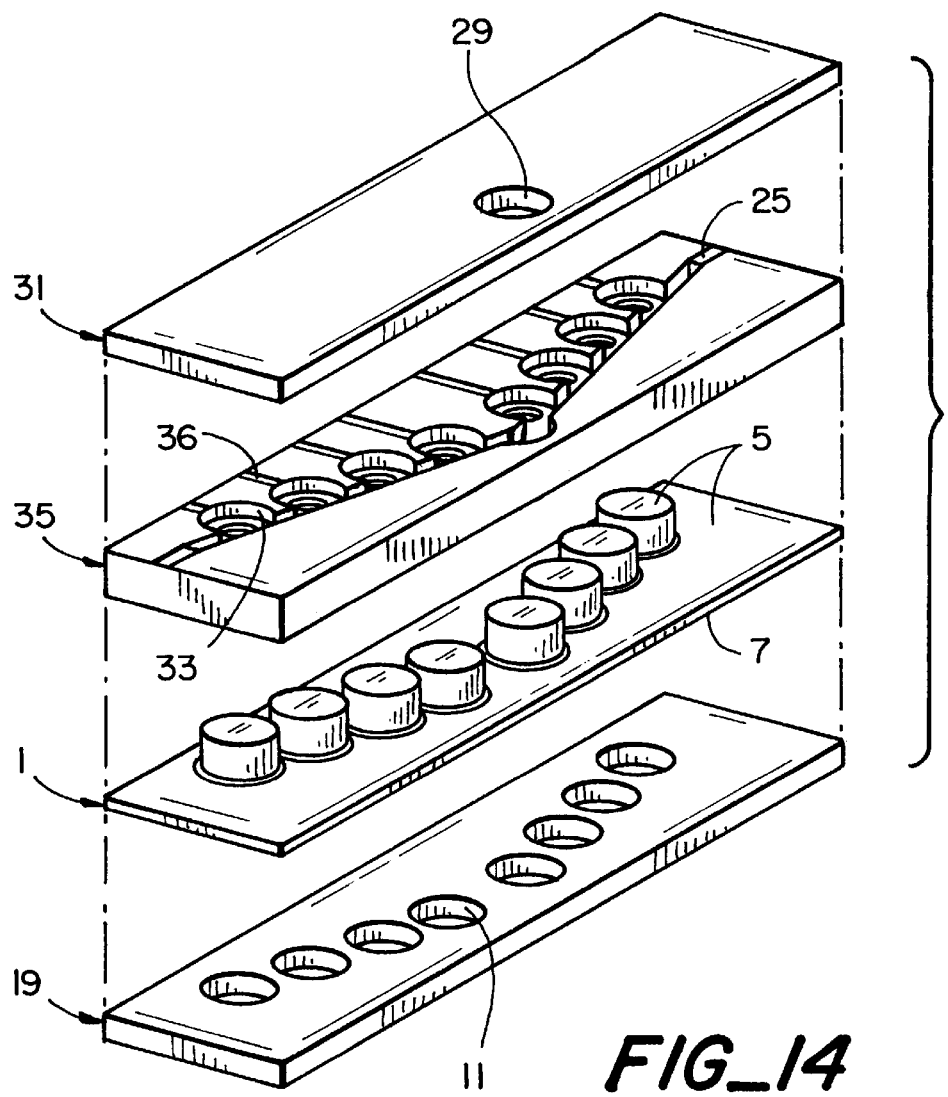
FIG_14
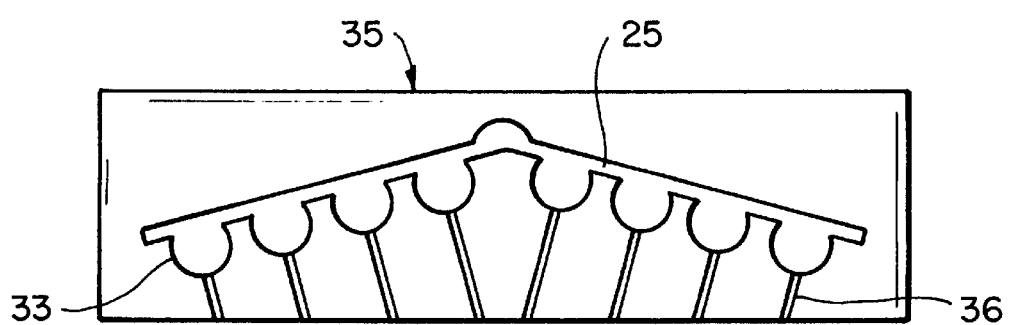
FIG_15

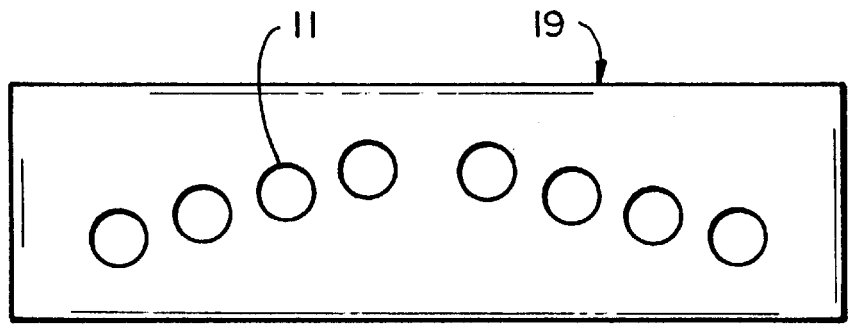
FIG_16
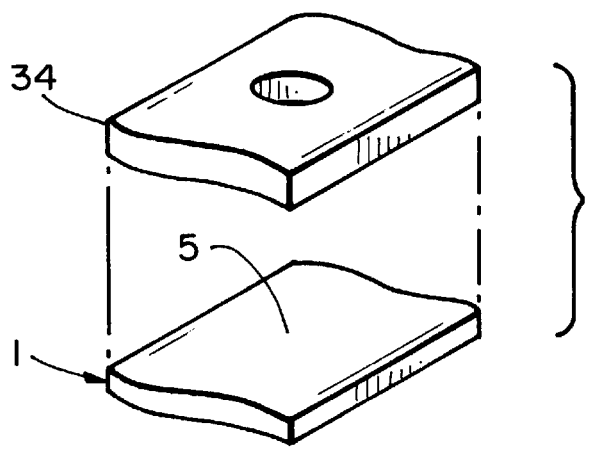
FIG_17
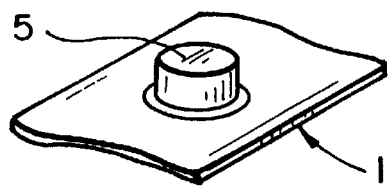
FIG_18

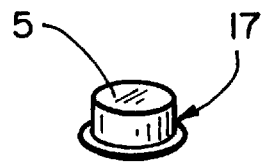
FIG_19
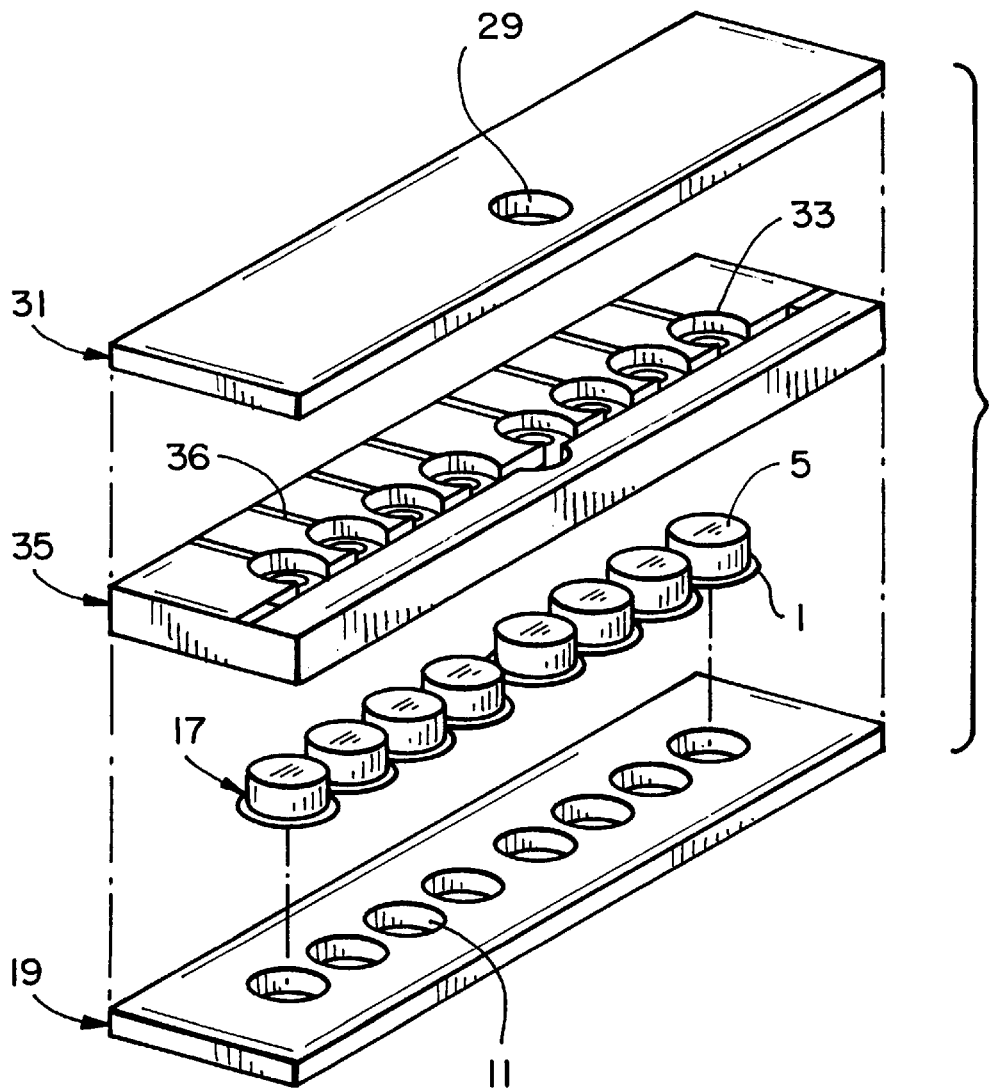
FIG_20

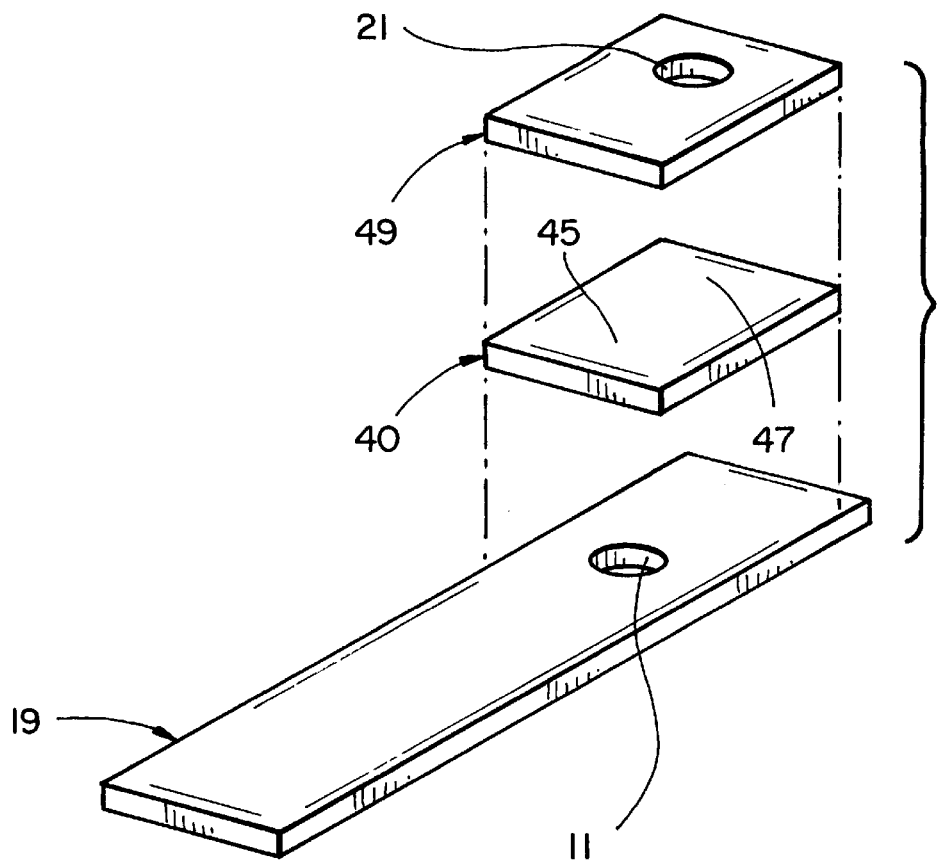
FIG_21
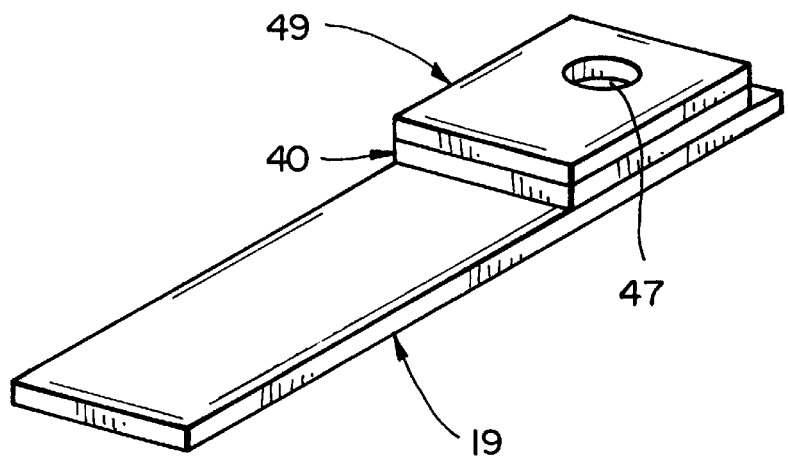
FIG_22

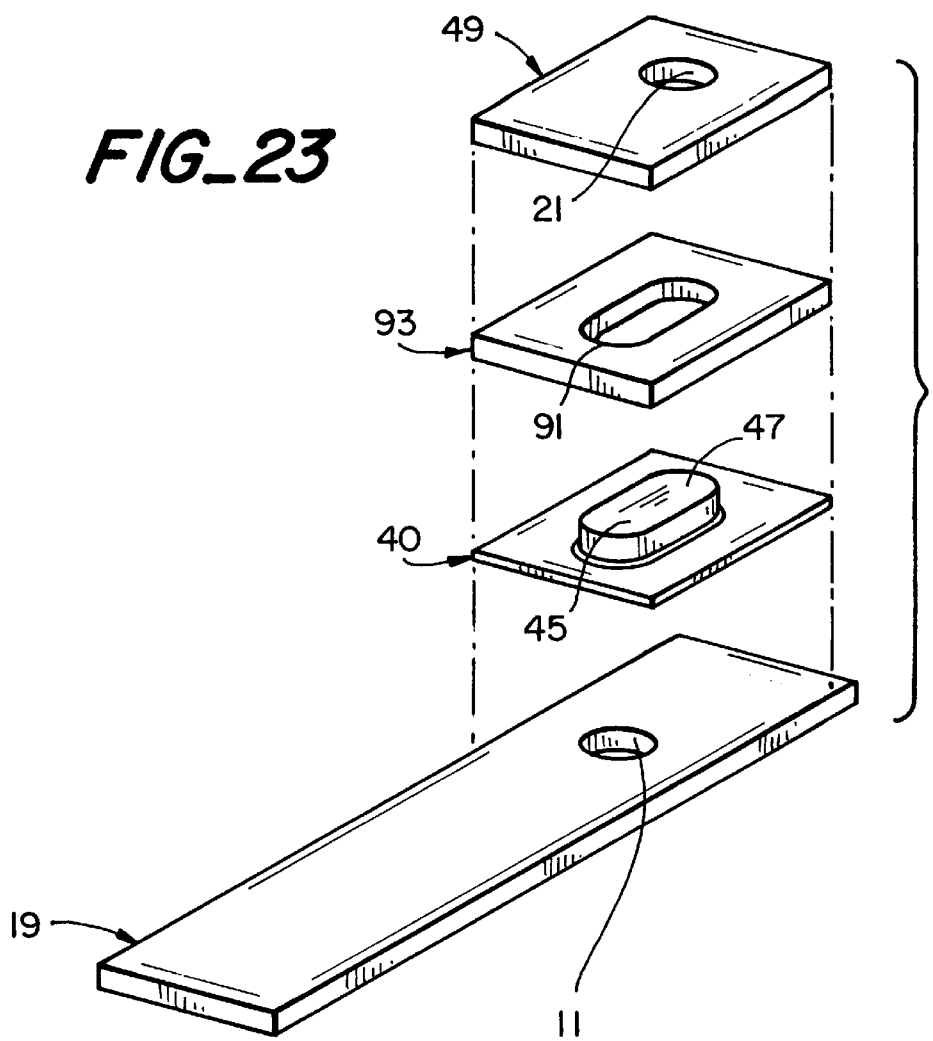
FIG_23
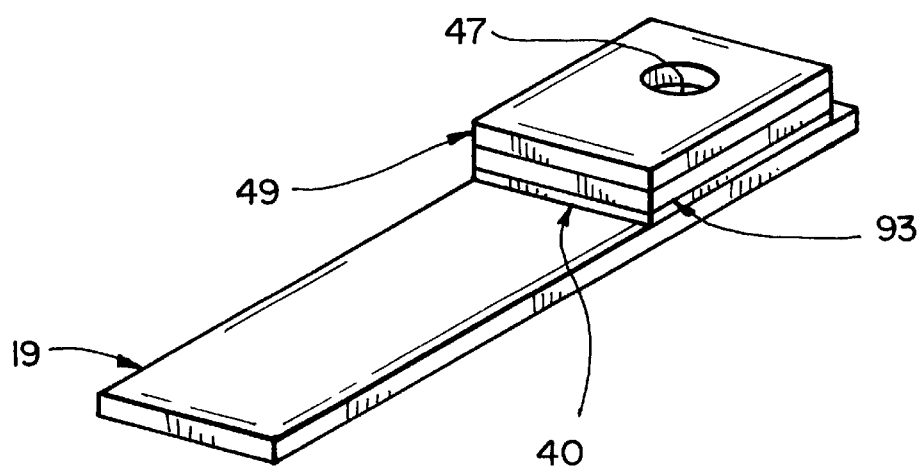
FIG_24

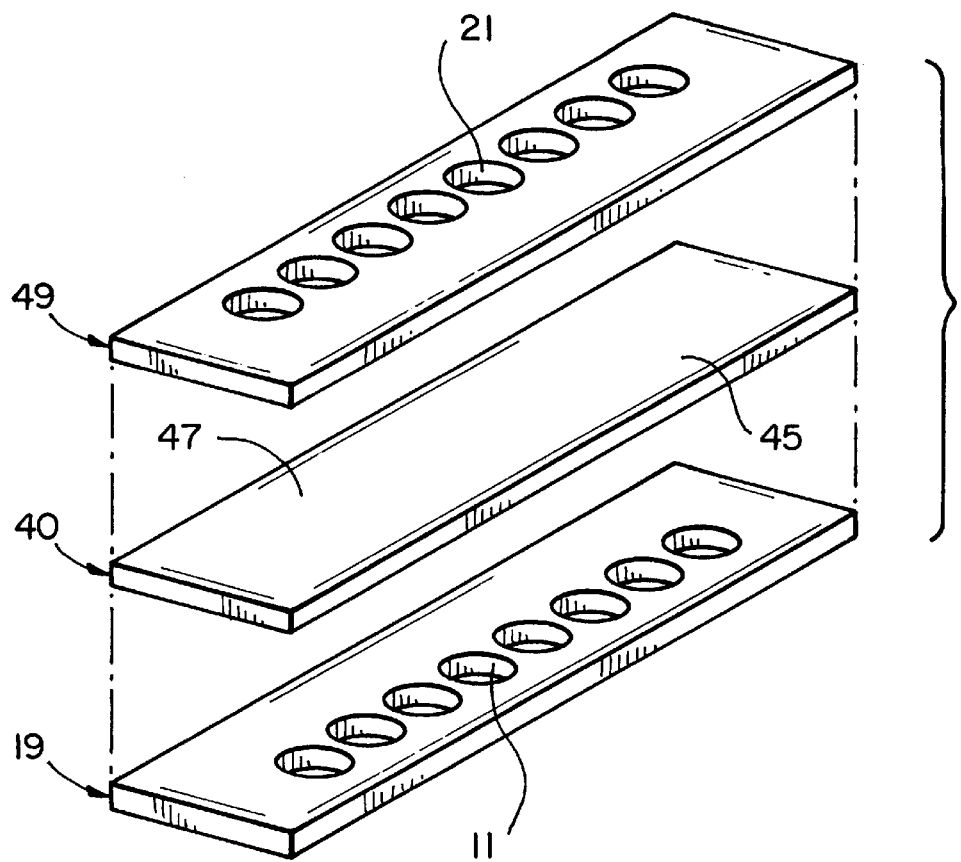
FIG_25
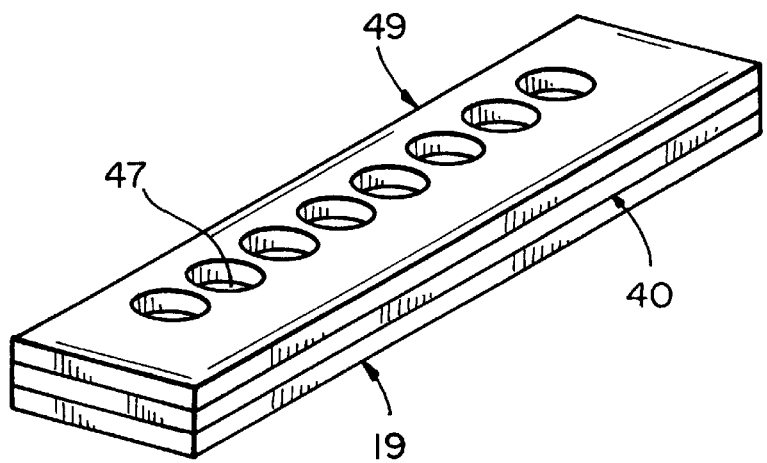
FIG_26

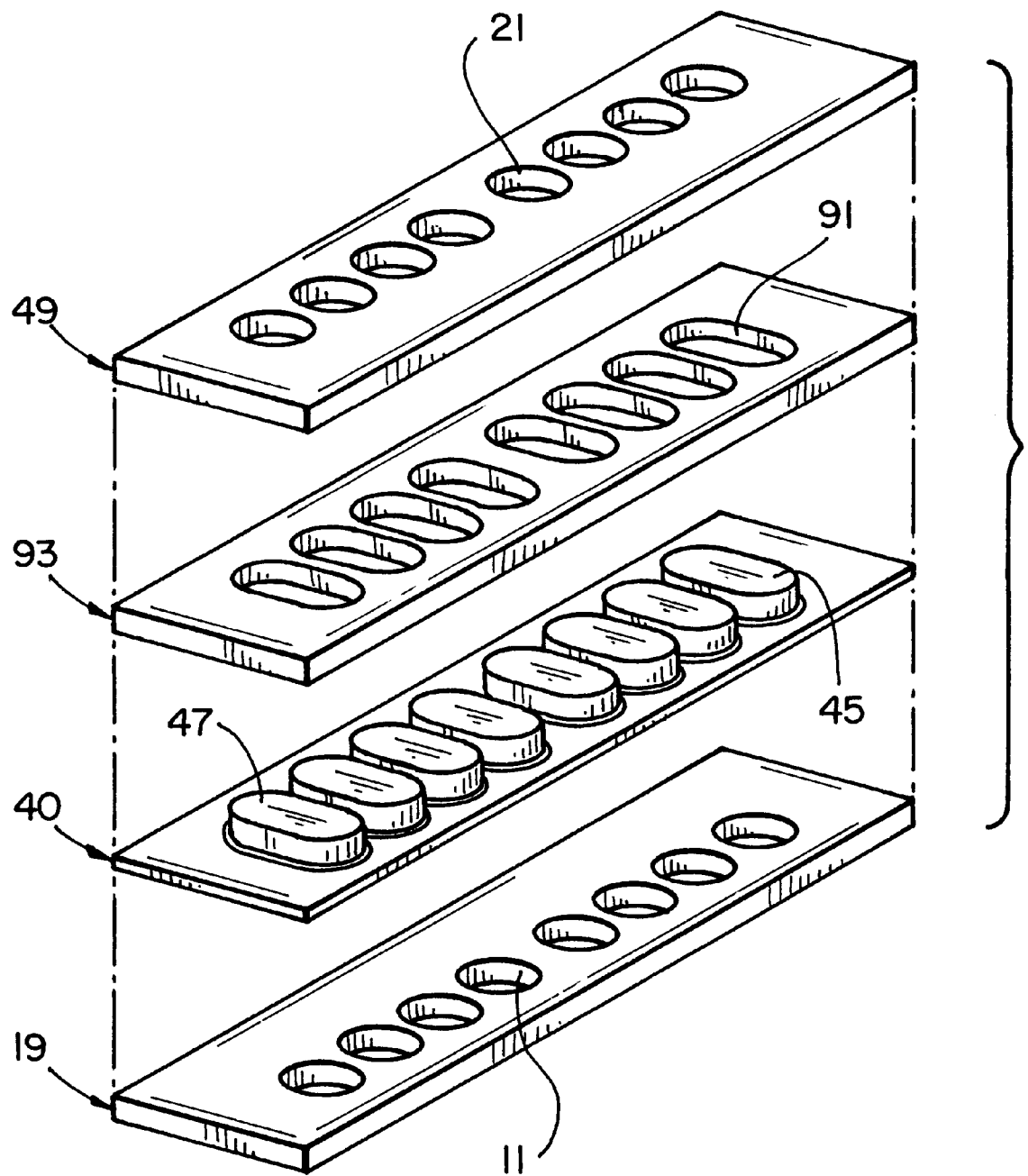
FIG_27

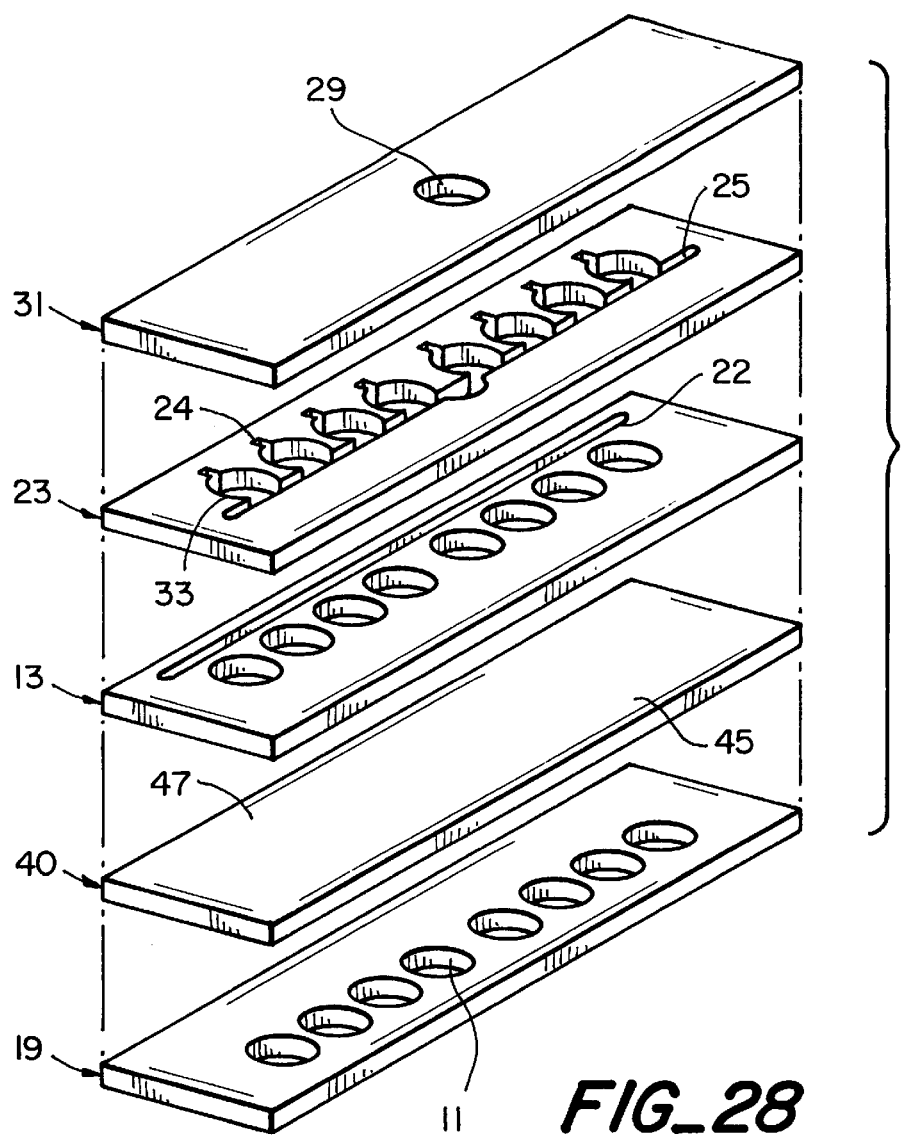
FIG_28
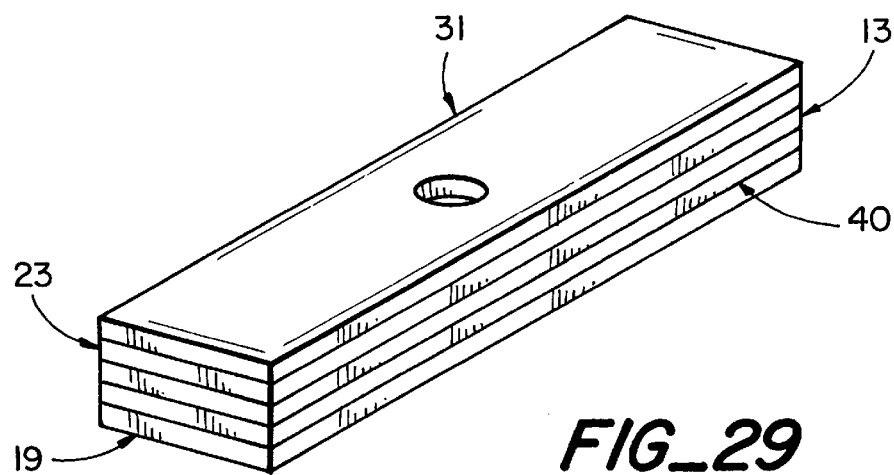
FIG_29

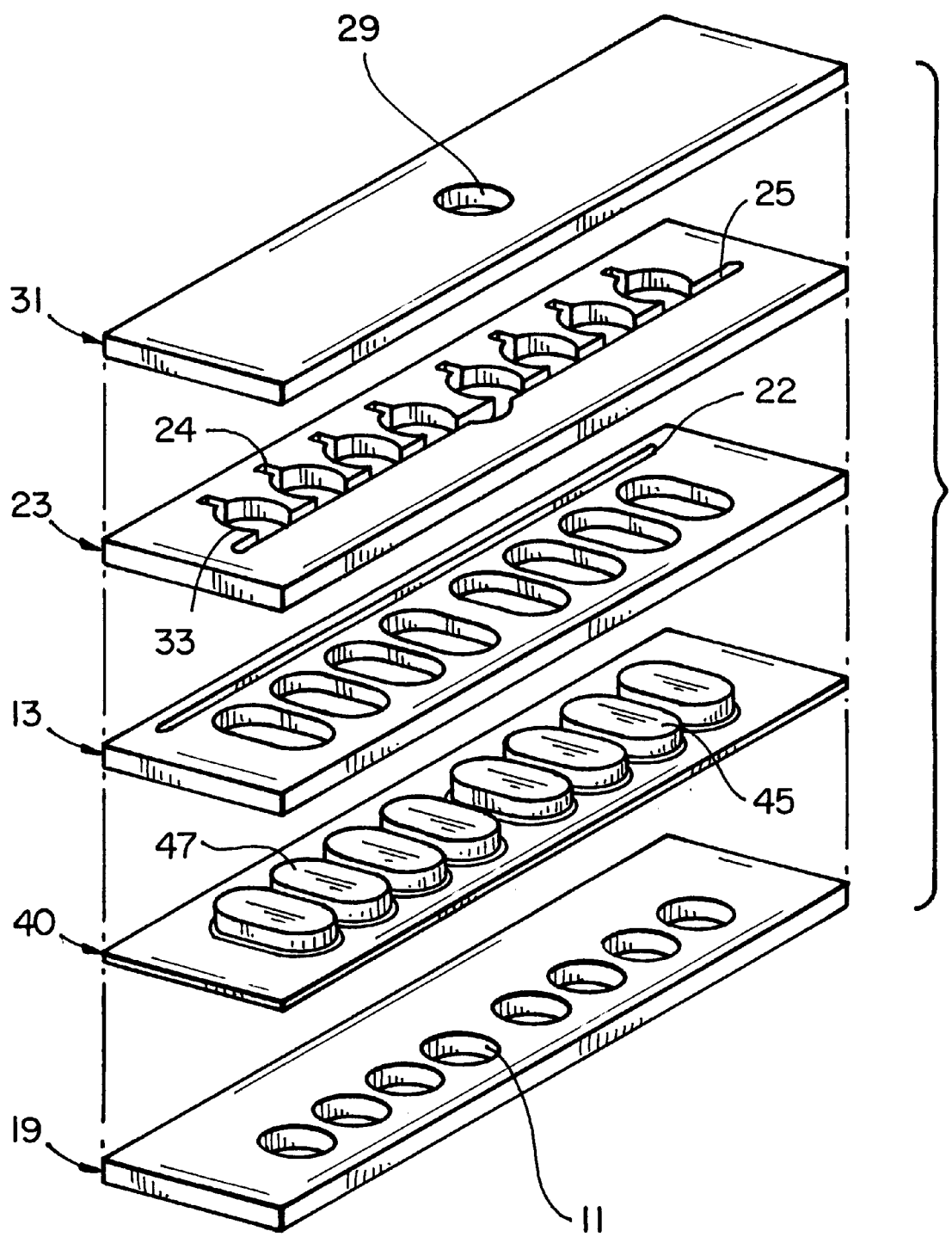
FIG_30

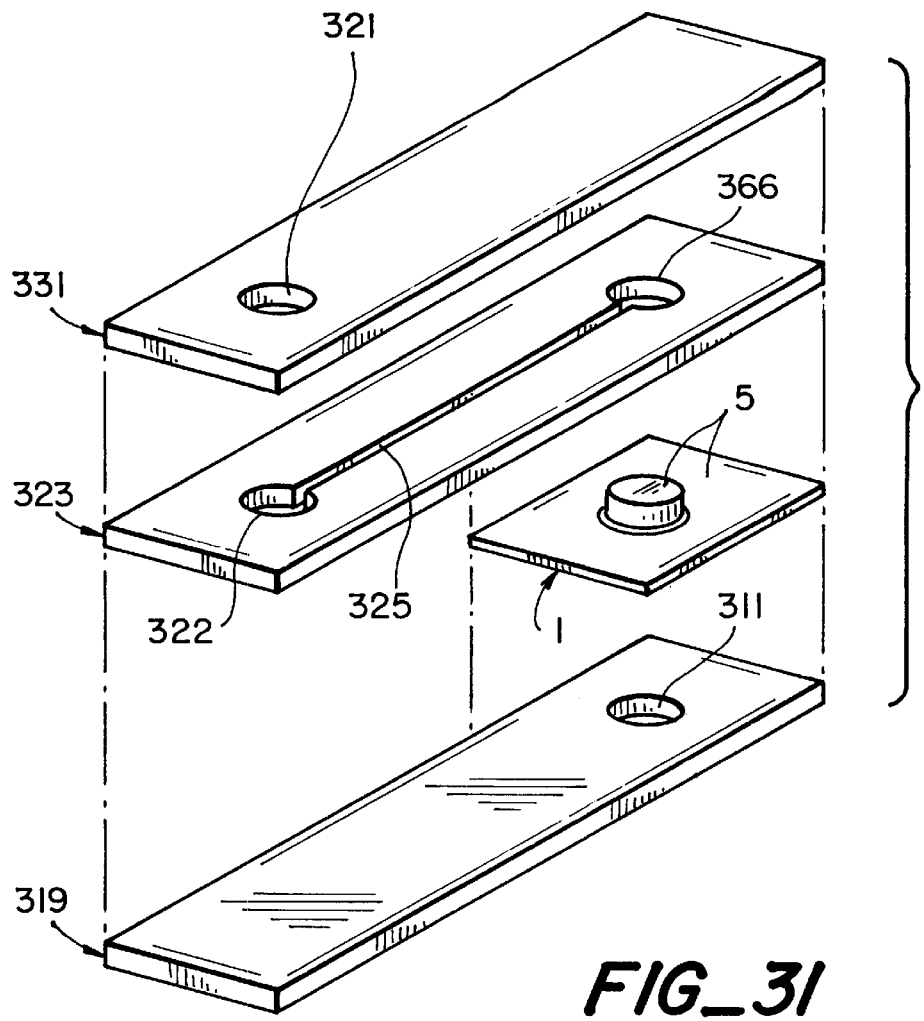
FIG_31
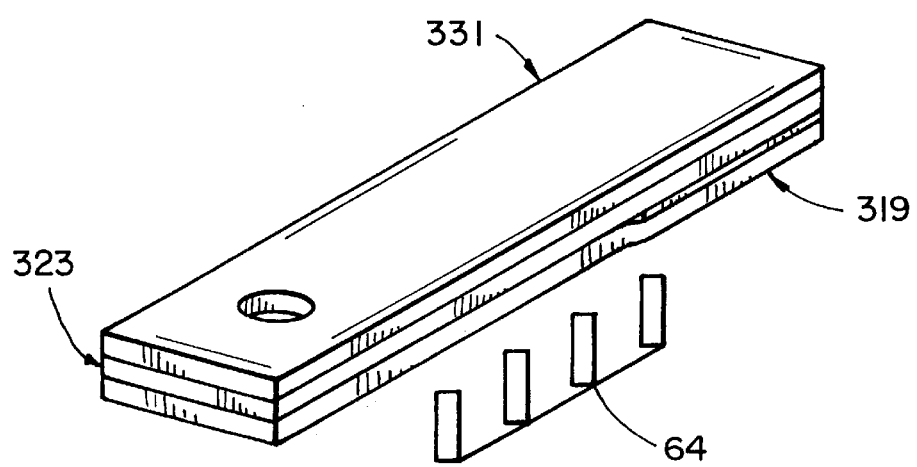
FIG_32

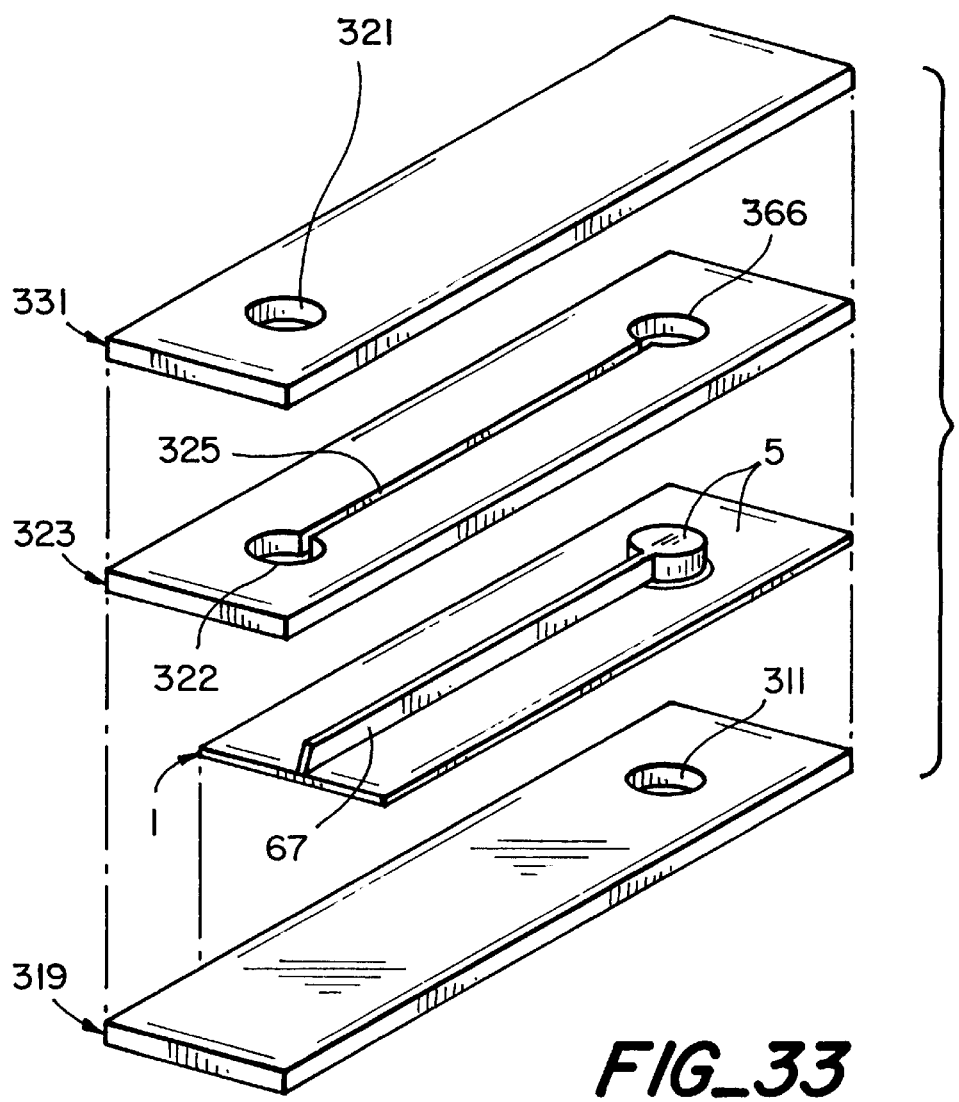
FIG_33
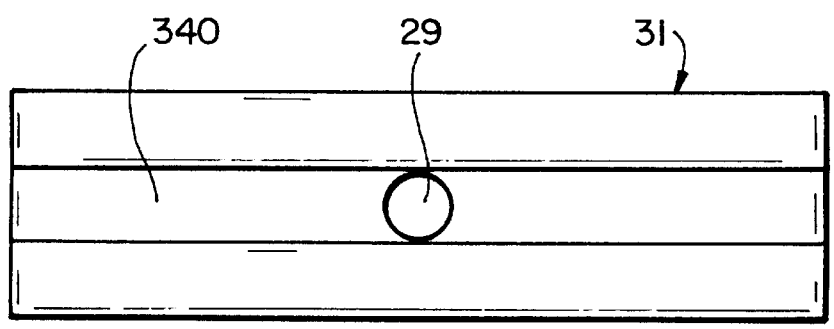
FIG_36

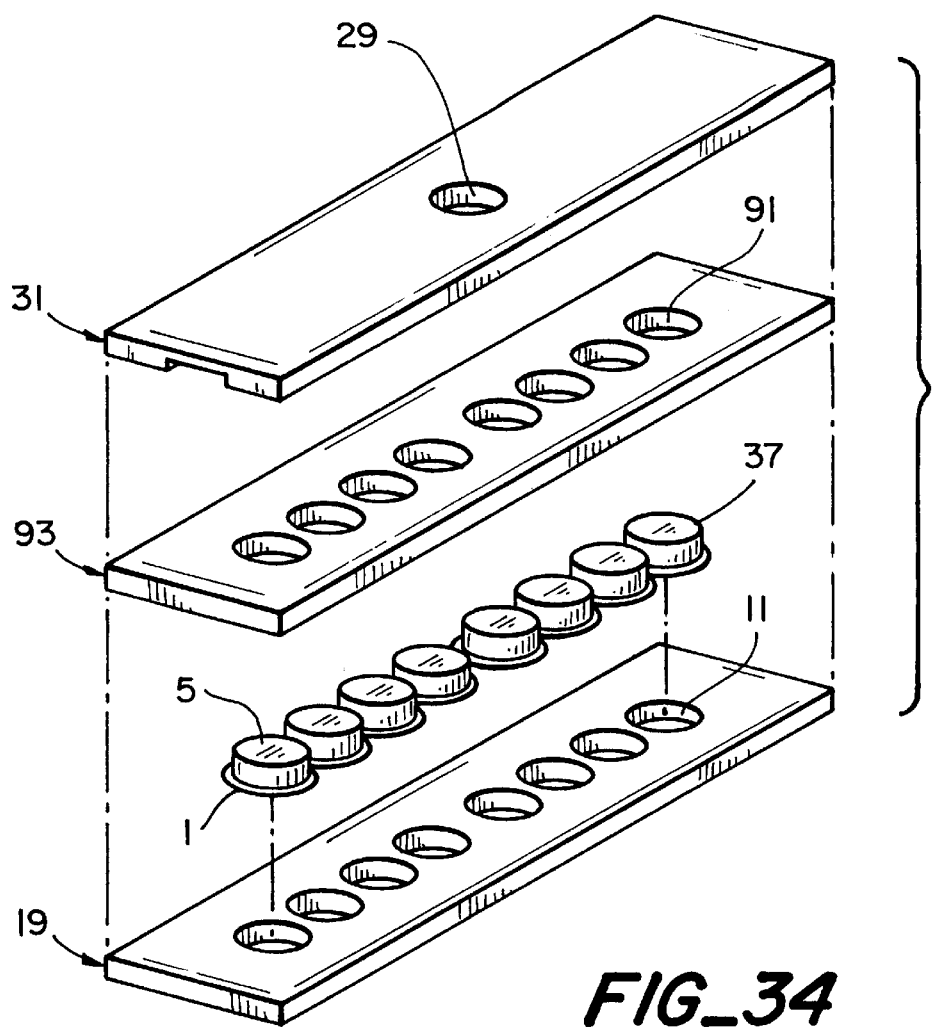
FIG_34
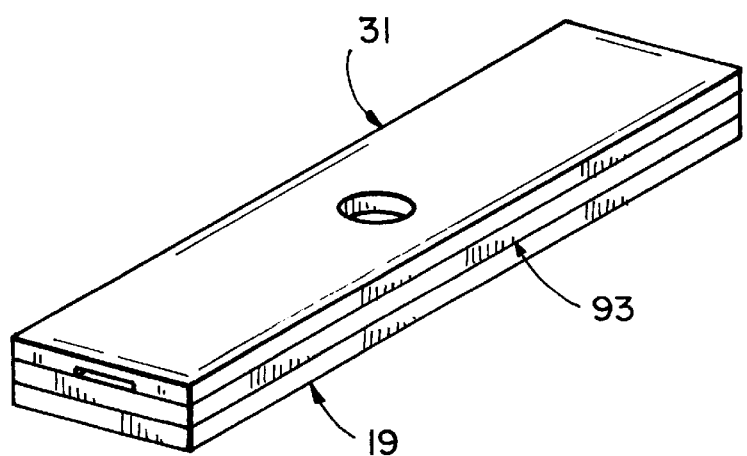
FIG_35

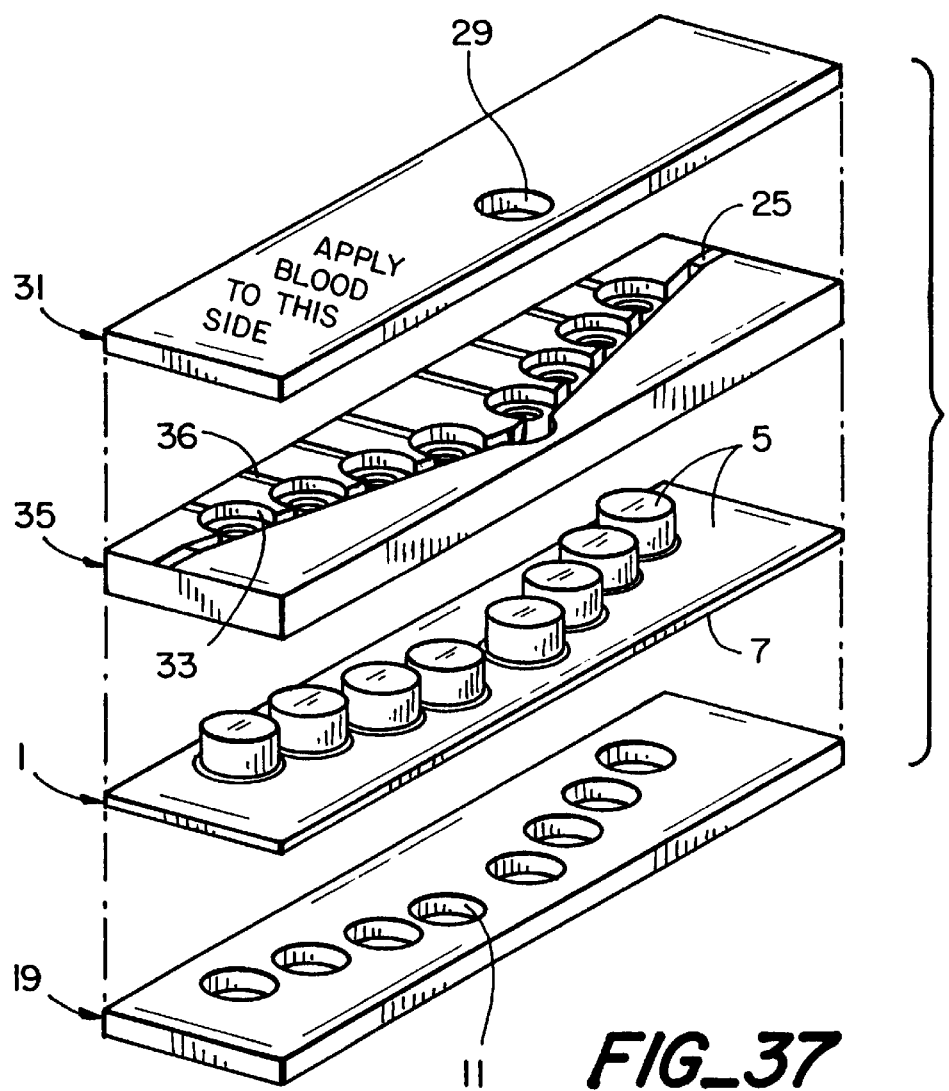
FIG_37
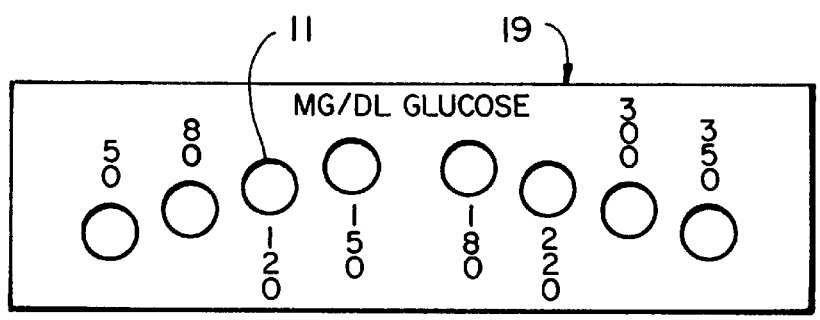
FIG_38

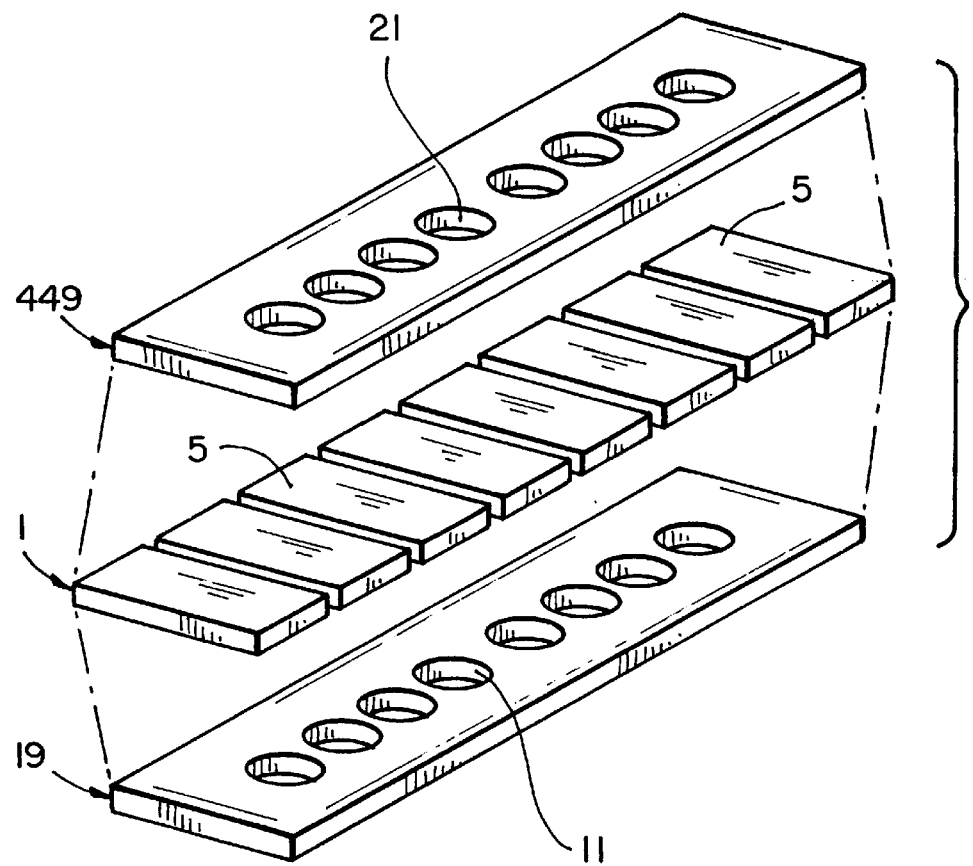
FIG_39
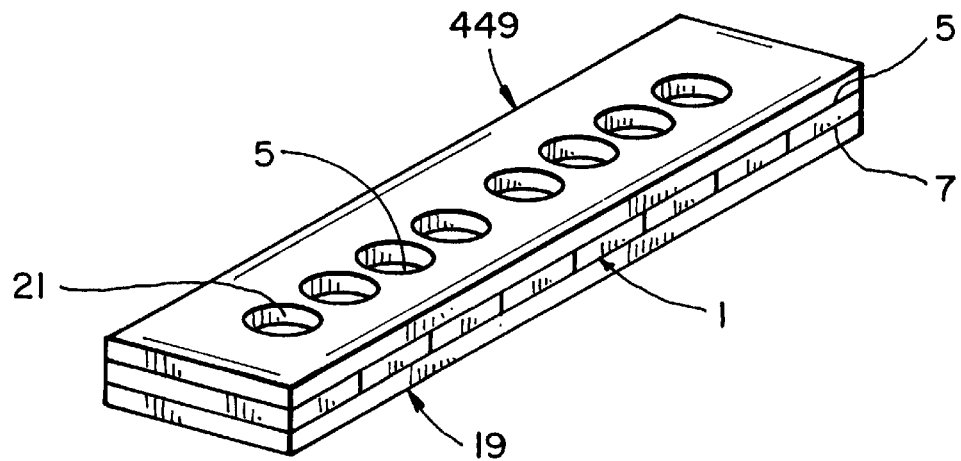
FIG_40

METHODS FOR TESTING THE CONCENTRATION OF AN ANALYTE IN A BODY FLUID

FIELD OF THE INVENTION

The present invention relates to a test device and method for the calorimetric determination of a chemical or biochemical component (analyte) in an aqueous body fluid, such as whole blood. In particular the present invention relates to a dry reagent test strip from which an analyte presence and/or concentration is determined by visual interpretation or through the use of an instrument. A common use of such test strips is for determination of glucose level in blood by diabetics.

BACKGROUND OF THE INVENTION

Numerous devices have been developed to test for presence and quantity of analytes in aqueous samples, such as whole blood or urine. The patent and technical literature of the last thirty years is replete with inventions which utilize a reagent strip containing a dry chemistry reagent system, that is, a system in which the wet chemistries are imbibed into an absorbent or bibulous medium, dried, and later reconstituted by fluid from the test sample. The reagent strips contain an indicator which changes color, depending on the presence or concentration of a particular analyte in a biological fluid applied to the strip. These strips may be read visually by reference to a color standard or calorimetrically by instrument calibrated or programmed to detect a certain color. Although some of these strips use reduction chemistries, more commonly they involve an oxidizable dye or dye couple. Some of the strips include an enzyme, such as glucose oxidase, which is capable of oxidizing glucose to gluconic acid and hydrogen peroxide. They also contain an oxidizable dye and a substance having peroxidative activity, which is capable of selectively catalyzing oxidation of the oxidizable dye in the presence of hydrogen peroxide. (See, for example, U.S. Pat. No. 5,306,623, to Kiser et al.) Examples of these devices, in addition to those used to test blood glucose, include tests for cholesterol, triglycerides, calcium or albumin in whole blood, and for protein, ketones, albumin or glucose in urine.

Dry chemistry reagent strips incorporating enzyme-based compositions are used daily by millions of diabetics to determine blood glucose concentrations. The NIH sponsored study, the Diabetes Complications and Control Trial, demonstrated conclusively that careful control of blood glucose levels can significantly reduce the incidence of serious complications of diabetes such as vision loss and kidney malfunction. Most diabetics must test themselves periodically in order to make appropriate adjustments to their diet or medication. It is thus especially important for diabetics to have rapid, inexpensive, and accurate reagent strips for glucose determination. The embodiment of dry chemistry reagent systems in test strips enable simple yet effective analytical protocols.

The technologies embodied in the products which have been developed to date have certain limitations from the perspective of the end user and/or the manufacturer. There is, therefore, a need to overcome some of the limitations of currently available colormetric testing systems.

U.S. Pat. No. 3,092,465, issued to Adams et al., U.S. Pat. No. 3,298,789, issued to Mast and U.S. Pat. No. 3,630,957, issued to Rey et al., all describe a basic reagent system which became a standard for colorimetric determination of glucose in biological samples. These patents describe the formation of a film layer or semi-permeable coating over the bibulous matrix to hold back the larger particulates, such as red blood cells, and allow fluid to permeate into the bibulous matrix. This approach requires the removal of red blood cells by washing or wiping to enable visual inspection or instrument reading of the indication of the dye color formed in the matrix.

Stone, U.S. Pat. No. 3,607,093, discloses a membrane for testing blood where the membrane has a skin permeable to solutions but impermeable to solids such as red blood cells and to macromolecules such as proteins. This membrane is disclosed as being used by applying a blood sample then wiping away the red blood cells from the skin in order to reach the test indication through the skin.

U.S. Pat. No. 3,552,928, issued to Fetter discloses the use of certain water soluble salts and amino acids in reagent formulations as separation agents to provide blood separation. With solids such as red blood cells substantially removed from the biological fluid, there is less background color at the test site to obscure a change in coloration produced by a testing reagent.

Phillips et al., U.S. Pat. No. 4,935,346 discloses a system wherein a whole blood sample is applied to the device and indicator development occurs in the presence of the colored components of the sample. Measurements of the color change in indicator are made at two distinct wavelengths to eliminate the interferences from the presence of colored blood components.

Kiser et al., in U.S. Pat. Nos. 5,306,623 and 5,418,142, disclose a visual meter device which incorporates various coatings on a matrix material to filter red blood cells from fluids. Similar devices for visual indication are disclosed by Hochstrasser in U.S. Pat. Nos. 3,964,871 and 4,059,407.

Terminello et al., U.S. Pat. No. 4,774,192, disclose a system in which the matrix is formed of an asymmetric material used to filter the red blood cells in the sample. The asymmetric material has a density gradient from one side to the other to progressively separate red blood cells from the fluids.

Daffern et al., U.S. Pat. No. 4,994,238, disclose a test device that comprises an asymmetric reagent layer that has progressively finer filtration with increased distance from one surface toward the other surface.

Castino et al., U.S. Pat. No. 5,456,835 disclose the use of filters formed of ligand modified polymeric film such as polypropylene fibers and polyethersulfone fibers.

Vogel et. al., U.S. Pat. No. 4,477,575, disclose the use of glass fiber material to achieve blood separation through the thickness of the material. Blood is applied to one side of the glass fiber, and relatively clear fluid migrates out of the opposite side. This fluid is delivered to an additional layer where the detection of analytes can occur.

Macho et al., U.S. Pat. No. 5,451,350, disclose the use of absorbent channels to distribute sample fluid in multi-zone test devices. Charlton et al., U.S. Pat. No. 5,208,163, also disclose the use of capillary channels to distribute blood to various chambers in the device.

The disclosures of the above patents are incorporated herein by reference.

The prior art devices and methods of the above references provide varying degrees of effectiveness of blood analysis at varying degrees of complexity and cost.

It is an object of the present invention to provide improved devices and methods to improve the performance and minimize the cost and complexity compared to the prior art devices.

It is a further object of the present invention to provide a fully disposable, discrete reading system for detecting analyte presence or concentration.

It is another object of this invention to provide a dry reagent chemistry system capable of analyzing whole blood for one or more analytes without prior separation of the red blood cells from the serum.

It is another object of this invention to provide a means for performing microtitration for the analysis of whole blood in a system which enables the ready visual determination of analyte presence or concentration.

It is yet another object of this invention to provide a blood separation system which can be used with a dry chemistry reagent to analyze whole blood for one or more analytes.

It is still a further object of this invention to provide a dry chemistry reagent and test strip which can be used in an electronic meter to analyze whole blood for one or more analytes.

The above objects as well as others are achieved by the devices, methods and systems of this invention as disclosed herein.

SUMMARY OF THE INVENTION

In one aspect this invention provides a method of testing blood for the presence or concentration of an analyte by using a porous matrix comprising a skin side and a test side, wherein the skin side comprises a porous skin capable of blocking the passage of red blood cells and of allowing passage of blood fluids containing an analyte to the test side of the matrix, and wherein the test side of the matrix is isotropic for uniform distribution therein of fluid received from the skin side and comprises an indicator capable of indicating the presence or concentration of the analyte. The method comprises applying a blood sample to the skin side of the matrix, allowing the fluid to pass through the skin into the isotropic matrix, then reading or measuring on the test side of the matrix the indication provided by the indicator of the presence or concentration of the analyte without removal of the red blood cells from the skin side of the matrix. The skin side is optionally treated with compounds which assist in blocking the passage of red blood cells and allowing passage of substantially clear fluid. Such compounds, or separating agents, can help facilitate the wicking of the clear fluid into the test side of the matrix. However, it is preferred that the skin side of the matrix is inherently hydrophilic which facilitates the passage of fluid through the skin to the test side of the matrix while blocking passage of the red blood cells. This separation of the blood on the skin side and reading or measuring the resultant indication on the test side of the matrix makes the determination of the presence and/or concentration of analyte simpler due to the relative absence of red blood cells at the test site of system and due to the absence of the necessity of removing the red blood cells before taking the desired reading or measurement.

In another aspect this invention provides a device for testing blood for the presence or concentration of an analyte comprising a holder comprising an opening for receiving a blood sample; and a porous matrix comprising a skin side and a test side wherein the skin is capable of blocking the passage of red blood cells and of allowing the passage of blood fluids containing an analyte to the test side of the matrix and wherein the test side of the matrix is isotropic for uniform distribution of fluid received from the skin side. The test side of the matrix comprises an indicator for indicating the presence or concentration of an analyte in the fluid. The matrix is attached to the holder so that the skin side is oriented toward the opening in the holder for receiving the blood sample such that when a blood sample is applied in said opening the blood contacts the skin side of the matrix allowing the blood fluids to pass to the test side of the matrix and red blood cells to be retained on the skin side of the matrix. The device can optionally have a support member applied to the test side of the matrix, where the support member has a visual opening through which the indicator is read or measured.

Alternatively, the support member can be a solid layer, and the holder can have a second opening through which the indicator can be read or measured after the fluid passes through the skin and into the matrix extending under the second opening in the holder. In this alternative, the skin side and the test side can be on the same side of the matrix member, but the skin providing the blockage of red blood cells is in a different area from the test area of the matrix. In such an alternative, an adequate seal is provided to prevent whole blood from flowing from the skin area to the test area but only allow blood fluids to pass through the skin to the test side or area of the matrix.

In another aspect this invention provides a method of making a device for testing blood for the presence of an analyte comprising providing a holder comprising an opening for receiving a blood sample and laminating to the holder a porous matrix comprising a skin side and a test side wherein the skin is capable of blocking passage of red blood cells and of allowing passage of blood fluids containing an analyte to the test side of the matrix and wherein the test side of the matrix is isotropic for uniform distribution of fluid received from the skin side. In this embodiment, the skin side of the matrix is in contact with the holder and the opening in the holder communicates with the skin on the skin side of the matrix.

In another aspect this invention provides a device for testing concentration of an analyte in a fluid sample comprising a first member comprising an opening having a predetermined volumetric size and a porous matrix member positioned within said opening in the first member for receiving an amount of fluid to fill the volumetric opening. The matrix member comprises an indicator capable of indicating the presence of the analyte, and the matrix member comprises a skin side and a test side wherein the skin side is capable of blocking the passage of solids present in the fluid and of allowing passage of fluid containing an analyte to the test side of the matrix positioned in the volumetric opening. It is preferred that the skin side of the matrix member is a material which is inherently hydrophilic and facilitates the passage of the fluid through the skin side to the test side of the member. The device can optionally have a support member with a visual opening at least in part aligned with the opening in the first member whereby the fluid sample can be applied to one opening, the skin can block passage of solids but allow passage of fluid to the test side of the matrix and the analyte can be detected in the test side of the matrix through the other opening. Sequentially or simultaneously the predetermined volumetric size of the opening in the first member provides for a quantitative measurement of the concentration of the analyte in the fluid by enabling titration of a known amount of indicator reagent and a given volumetric quantity of fluid containing the analyte and the color indicator provides a qualitative indication. This invention further comprises methods of using these devices to quantitively measure an analyte in a fluid.

In another aspect this invention provides a method of making a device for testing concentration of an analyte in a fluid comprising providing a first member being substantially noncompressible and having an opening therein of a predetermined volumetric size and providing a porous matrix member which is fluid permeable and is compressible compared to the first member. The method comprises pressing the matrix member against the first member so that a portion of the matrix member protrudes within said opening and a portion of the matrix member is compressed against the surface of the first member adjacent to said opening. Optionally, a support member with an opening aligned with the opening in the first member can be laminated to the first member to position the compressed portion of the matrix between the first member and the support member. Also, optionally the compressed portion of the matrix member can be removed leaving the portion of the matrix member within the opening. The matrix member used in this method of making such devices optionally can have a skin side wherein such a matrix member is positioned in the devices as described above wherein the skin side protrudes into said opening or the skin side faces the support member.

In another aspect this invention provides a device for the testing for the presence or concentration of an analyte in a fluid sample comprising a first member comprising an opening for receiving a fluid sample, a porous matrix member positioned in communication with and extending laterally from said opening in the first member, where the matrix member comprises an initial area, which is in communication with the opening in the first member, and a test area, which is a given distance laterally from the initial area. The matrix member contains pores which are capable of blocking in the lateral distance between the initial area and the test area the passage of solids in the fluid sample and capable of allowing passage of fluid the lateral distance from the initial area to the test area of the matrix. The test area of the matrix comprises an indicator capable of indicating the presence or concentration of the analyte. This device can optionally comprise a support member comprising an opening therein on which support member the first member and the matrix member are mounted so that the matrix member is positioned between the first member and the support member and so that the opening in the support member is offset from the opening in the first member and is positioned over at least a portion of the test area of the matrix. This device is capable of receiving a fluid through one opening at the initial area of the matrix, allowing the fluid to pass laterally through the matrix from the initial area of the matrix to the test area of the matrix while the pores of the matrix provide blocking of the passage of solids. The other opening at the test area of the matrix is a visual opening which allows detection of the indication of the indicator. Alternatively, the second opening at the test area of the matrix member can be in the first member at the given lateral distance from the opening at the initial area of the matrix. The optional support member may be solid with no openings. In this alternative device, the fluid sample is received in the first opening at the initial area and the indicator read at the second opening at the test area where both openings are on the same side of the device.

In the above embodiments utilizing lateral flow of the fluid, an anisotropic or asymmetric porous matrix can be used. For example, in such a matrix separation of solid components can occur based on decreasing or changing pore size in the matrix. However, in such embodiments an isotropic porous matrix may be employed where uniform sized pores block the passage of solids. In either case, the solids such as red blood cells, introduced at the initial area of the matrix can be held back from the test area of the matrix. If the solids are not adequately blocked and are allowed close to the test area, the solids may cast a shadow or cause color difference in the test area of the matrix. In such cases compensation may need to be made in the reading of the indicator.

In another aspect this invention provides a device for testing for the presence or concentration of an analyte in a fluid sample comprising a member having a first opening for receiving a fluid sample and a second opening for receiving fluid from the first opening wherein the first opening and the second opening are connected by a restricted flow passageway or delivery channel communicating with the first opening and second opening thus enabling the fluid sample to flow from the first opening to the second opening through the restricted flow passageway. This device further comprises a detector for detecting and measuring the rate of initial flow of the fluid from the first opening through the restricted flow passageway towards the second opening. This aspect of the invention also provides a method of using such device wherein the rate of initial flow of fluid through the restricted passageway is measured and correlated to the concentration of a particular concentration of solids (e.g., hematocrit level) in the fluid sample. It has been found that the rate of initial flow of fluid through the restricted flow passageway can be directly correlated to the concentration of an analyte and the fluid. Optionally, in this aspect of the invention the second opening may contain a porous matrix positioned in the second opening comprising an indicator for indicating the presence or concentration of an analyte in the fluid sample entering the matrix. Also, optionally, the porous matrix positioned in the second opening may comprise a skin side and a test side as described above in connection with other embodiments of this invention. In this aspect of the invention the measurement of the rate of initial flow of the fluid through the restricted flow passageway can also be correlated to the indication provided by the indicator in the matrix in the second opening thus providing more complete information with respect to the hematocrit level of the fluid. Also optionally a matrix material may be present in the restricted flow passageway or delivery channel, and the initial flow rate therethrough can be correlated to an hematocrit level of the blood as described above.

The above embodiments of the devices of the invention with the appropriate dry chemistry system in the matrix member can be used in test strips which may be read visually or measured in an electronic meter. Electronically read devices or strips are provided with appropriate calibration data and test initiation sequences which can be incorporated on the strips in the form of bar codes, digital punches, magnetic signals or the like. These codes or signals on the test strips provide appropriate data to the meter and eliminate the need for inputs from the user. These aspects simplify the test protocol and reduce the potential for user generated error.

The above sets forth the generic aspects of the various devices and methods of the present invention. These devices and methods are more fully described in the drawings and the descriptions below.

BRIEF DESCRIPTION OF THE DRAWINGS

FIG. 1 is a perspective exploded view of a matrix member and a member having and opening for receiving a fluid.

FIG. 2 is a perspective view of the device of FIG. 1 assembled.

FIG. 3A shows an electronic meter receiving a device of FIG. 2 and a drop of fluid entering the device of FIG. 2.

FIG. 3B shows an example of machine readable coding on the device of FIG. 2

FIG. 4 is a perspective exploded view of a matrix member positioned between a first member and a support member, where the device comprises a plurality of test sites for one analyte or multiple analyte tests.

FIG. 5 is a perspective view of the device of FIG. 4 assembled.

FIG. 6 is a perspective exploded view of a device having a plurality of test sites for one or more analytes and a delivery channel for delivering fluid from a central sample introduction point to a plurality of test sites.

FIG. 7 is a perspective view of the device of FIG. 6 assembled.

FIG. 8A is a perspective exploded view of a matrix member partially compressed and partially protruding into an opening in a noncompressible member.

FIG. 8B is a perspective exploded view of a matrix member partially compressed between a first member and a support member and partially protruding into an opening in the first member.

FIG. 9 is a perspective view of the device of FIG. 8B assembled.

FIG. 10A is a perspective exploded view of the device of FIG. 8B having a plurality of test microtitration sites for one analyte or multiple analyte tests.

FIG. 10B is a perspective view of the device of FIG. 10A assembled.

FIG. 11 is a perspective view of a partially compressed matrix with rounded protrusions for extension into openings.

FIG. 12 is a perspective exploded view of a device of FIG. 10A having a plurality of microtitration test sites for one or more analytes and a delivery channel for delivering fluid from a central sample introduction point to a plurality of test sites.

FIG. 13 is a perspective exploded view of the device of FIG. 12 assembled.

FIG. 14 is a perspective exploded view of the device of FIG. 12 wherein the test sites are arranged to provide gravity-aided flow of the fluid sample to the test sites. FIG. 15 is a schematic diagram of the capillaries and test sites of the device in FIG. 14.

FIG. 16 is a schematic diagram of the openings in the device in FIG. 14.

FIG. 17 is a perspective view of a noncompressible member having an opening which can be pressed together with a compressible matrix member to partially compress the compressible matrix member and cause the protrusion of a portion of a matrix member into the opening of the noncompressible member.

FIG. 18 is a perspective view of the partially compressed matrix member after removal from the noncompressible member.

FIG. 19 is a perspective view of a shaped matrix insert formed by removal of the compressed portion of the article of FIG. 18.

FIG. 20 is a perspective exploded view of a device having a plurality of individual matrix inserts of FIG. 19 placed in openings in a first member having a delivery channel for delivering fluid to each of the openings from a central sample introduction point.

FIG. 21 is a perspective exploded view of a matrix member positioned between a first member having an opening and a second member having an opening offset from the opening in the first member.

FIG. 22 is a perspective view of the device of FIG. 21 assembled.

FIG. 23 is a perspective exploded view of a matrix member partially compressed and partially protruding into an opening in a noncompressible member positioned between a first member having an opening and a second member having an opening offset from the opening in the first member.

FIG. 24 is a perspective view of the device of FIG. 23 assembled.

FIG. 25 shows a device according to FIG. 21 having a plurality of test sites for one analyte or multiple analyte tests.

FIG. 26 is a perspective view of the device of FIG. 25 assembled.

FIG. 27 is a perspective exploded view of the device of FIG. 23 having a plurality of test sites for one analyte of multiple analyte tests.

FIG. 28 is a perspective exploded view of the device of FIG. 25 having a delivery channel for delivering fluid from a central sample introduction point to a plurality of test sites.

FIG. 29 is a perspective view of the device of FIG. 28 assembled.

FIG. 30 is a perspective exploded view of the device of FIG. 27 having a delivery channel for delivering fluid from a central sample introduction point to a plurality of test sites.

FIG. 31 is a perspective exploded view having a flow rate determinative delivery channel from a sample introduction opening to an opening containing an optional matrix member.

FIG. 32 is a perspective view of the device of FIG. 31 assembled and optical detectors for measuring the flow rate of fluid moving through the delivery channel.

FIG. 33 is a perspective exploded of the device of FIG. 31 wherein the delivery channel contains a matrix member.

FIG. 34 is a perspective exploded view of a device similar to FIG. 20 wherein the delivery channel is formed on the backside of the member containing the sample introduction opening.

FIG. 35 is a perspective view of the device of FIG. 34 assembled.

FIG. 36 is a bottom view or view of the backside of the member containing the sample introduction opening and showing the delivery channel in the device of FIG. 34.

FIG. 37 is a perspective view of a test strip of FIG. 14 and showing user instruction on the back of the strip at the blood application point.

FIG. 38 is a front view of the test strip illustrated in FIG. 37 showing user indicia for indicator readings.

FIG. 39 is a perspective exploded view of the device of FIG. 4 containing an individual or discrete matrix member for each fluid receiving opening and test site.

DETAILED DESCRIPTION OF THE INVENTION

The devices of the present invention are simpler to use and are easier and less costly to manufacture than most devices previously available. This is especially important for diabetics who rely on blood glucose testing multiple times per day to keep their disease under control. For many diabetics, the costs associated with blood glucose monitoring are significant, especially elderly diabetics on fixed incomes. Devices of various configurations and various uses based on the embodiments of the invention disclosed herein can be delivered to the diabetic patient, in a more cost effective manner. The ease of use and portability of these devices, coupled with more attractive pricing, will facilitate increased patient compliance with recommended testing routines and will result in improved overall health of diabetic patients.

In one or more aspects this invention uses an intrinsically hydrophilic membrane and takes advantage of and enhances the blood separation capabilities of such a membrane. This invention includes separating the whole blood and employs a microtitration system so that the separated clear fluid can be analyzed independently of the red blood cells. This segregation or isolation from the red cells of the clear fluid being analyzed is necessary to eliminate interferences from the highly colored cells and provide a more consistent liquid sample for the titration of the analyte by eliminating the majority of the blood solids from the test area. The red blood cells can mask the color indication of the indicator reagent making it difficult or impossible to read. If whole blood is absorbed into the test areas, volumetric differences due to varying solids content in the blood affect the titration sample size which can result in an inaccurate measurement of the analyte. By separating whole blood according to this invention into red blood cells and substantially clear fluid, an accurate analysis can be obtained on both a qualitative and quantitative basis. As used herein, reference is primarily made to blood. However, other fluids such as urine, saliva and the like can be analyzed utilizing the various embodiments of the present invention.

The invention uses membranes from two categories. The first category includes microporous membranes which separates the blood solids from blood fluids. The most preferred microporous membranes are polyethersulfone polymeric membrane which is formed with a skin side which acts as a red blood cell barrier and a matrix side which has uniform pore size for containing indicator reagents. The second category includes cellulose glass fiber composites or polymer based membrane or matrix products which facilitate lateral wicking of fluid and provide separation of blood solids from blood fluids. Vertical separation occurs perpendicular to the application side, through the depth of the material. Lateral separation occurs within the membrane parallel to the surface of the application side. In either category, this invention provides devices which avoid the necessity for meter reading. Due to the separation of red blood cells, these devices provide reliable visual reading of the indicator by the user. The improved separation and visual reading is in part provided by the devices of this invention where the blood solids and red blood cells are maintained in a floating state on the skin side or in some cases in the lateral matrix, which assists in keeping the color from the solids and cells from contaminating the test areas where visual reading of the indicator is desired.

The first membrane type can be treated with separation agents and test reagents. In a preferred embodiment, the membrane is inherently hydrophilic, has a smooth skin side and a rough matrix side which is an isotropic porous matrix. The whole blood is applied to the skin side and the combination of skin characteristics, hydrophilic matrix and separation agents hold the red blood cells on the surface of the skin side while clear fluid and analytes flow into the matrix. The key is that the whole blood must be delivered from the skin side to achieve proper separation. This mechanism creates a titration area in the matrix area free of red blood cells and containing a consistent volume of relatively clear fluid. The hematocrit effect normally found in dry chemistry tests is minimized as long as adequate clear fluid is provided (by the highest hematocrit blood specified) to rehydrate the indicator reagents while the red blood cells are blocked by the skin from entering the matrix. A reservoir is preferably provided for the sample so that upon separation of whole blood and relatively clear fluid, a large enough volume of fluid is provided to the solids in the matrix so they are fully hydrated, even with a high hematocrit blood where some excess of fluid remains on the skin surface of the membrane or within the reservoir.

The membrane of the first type are preferably a polyethersulfone polymer which is cast to inherently have a microporous skin on one side and a porous matrix on the other side, such as the Gelman membrane. However, one may also employ a matrix layer having uniform porosity but no barrier skin on either side by laminating to one side of such a matrix a microporous barrier film to form the required barrier skin on one side of the matrix.

Membranes of the second type are also preferably treated with separation and test reagents. The whole blood is applied to an initial area of the matrix, and the matrix wicks the fluid laterally to a test area of the matrix. As it wicks out, the separation reagents enhance the separation of the whole blood into red blood cells and relatively clear fluid. The matrix is preferably a naturally hydrophilic material. As the blood separates, clear fluid moves from the initial zone into the test zone and reacts with the indicator reagents to indicate the presence and concentration of analyte. The test zones must be positioned such that clear fluid migrates into the zones without red blood cells. In other words, for the highest hematocrit blood specified, there must be enough clear fluid to migrate to the test area to activate and react with the indicator reagent system. This invention minimizes the hematocrit effect observed in some test devices. Providing a uniform and adequate sample volume assures a uniform hydraulic head at each test site. The quantity of relatively clear fluid is such that, although the reservoir contains both red blood cells and clear liquid, the test volume supplied is the proper volume of sample for testing.

The invention provides different mechanisms for using the dry chemistry reagent systems with and without microtitration volume control. The dry chemistry components and microtitration principles are described below, independent of the embodiments which follow.

The microtitration concept employed in some aspects of this invention can be explained as a method of controlling the sample volume and the reagent amount to give a consistent titration and therefore consistent and reliable results. The first step is to create a test zone which is bounded. The traditional wet chemistry analysis uses a fixed (premeasured) volume of sample and titrates a quantity of test reagent against that sample. In a dry format the quantity of the test reagent has to be impregnated into the matrix in a ratio proportional to the void volume of the matrix. This can be accomplished many different ways. The sample volume (SV) is the void volume of the matrix (VVM) minus the solids volume remaining in the matrix from the test reagent following wet application and drying or test reagent volume (TRV). The ratio SV/TRV must be constant to provide an accurate titration.

To achieve microtitration the material void volume and the reagent application must be controlled. The device of this invention creates a fixed control geometry which does not permit cross talk between test areas and the sample delivery channel. The microporous membrane has a tendency to wick laterally, which the device in this aspect of the invention prevents. The whole blood is delivered so that it enters the test area matrix from the skin side of the microporous material. The sample may be introduced in any orientation to the laterally wicking materials which may alternatively be employed. The glass fiber material becomes quite fragile when fully wetted. Therefore, it is practical to only impregnate reagents in the test zones. This can be accomplished by using a syringe or needle to discretely apply the reagents in the test area. The most effective way to do this is to preassemble the device and coat the reagents while the cellulose and glass fiber is supported by the front panel of the test strip device. The other materials can be impregnated into the matrix either locally or by general application but in a controlled fashion.

In this invention, the preferred method for controlling the test area geometry is to emboss the membrane into the gasket or molded part, deforming a portion of the membrane into openings in the gasket or molded part and leaving the test areas uncompressed and compressing a portion of the membrane. The compressed areas are fastened to the gasket with adhesive such as 3-M grade 415 acrylic pressure sensitive adhesive, creating test areas which are completely bounded on the sides which prevents any flow between. The only means of sample entry into each opening is through the top, i.e., the skin side (e.g., see FIG. 10A). The membrane is embossed into the gasket by bringing both pieces together between two platens of a hydraulic press which pushes a portion of the membrane into the gasket openings and deforms the material outside of the openings by compressing it so that the thickness is reduced by 80 to 95% in the compressed area. (See FIG. 8B)

The material which is embossed can be die cut and the compressed area removed (in a process similar to creating a label on a printing press, see FIGS. 17–19) to eliminate any chance for cross talk between test zones. In this embodiment the test zones are held to the device only by a small ring of adhesive; the majority of the embossed or compressed material having been removed. The adhesive seals to the gasket member into which the die cut matrix inserts are inserted thereby preventing any leakage of fluid between test zones.

A second method can be utilized to create the microtitration zones. This method, shown in FIGS. 8A and 8 B, is also similar in concept to creating labels. An individual microtitration zone is attached to a viewing window or is captivated in a gasket. Adhesive is applied to a nonporous element in the area where the test zone is desired. A viewing window is punched in the nonporous member leaving an annular ring of adhesive. A sheet of membrane is applied to the part and laminated to the nonporous member at the adhesive rings. A die then cuts the membrane around the viewing hole and slightly greater in diameter than the adhesive ring. The unattached membrane is peeled away, leaving the test zones attached to the nonporous member at the viewing windows. (See FIG. 20.)

The sample can enter the microtitration zones via openings in a gasket layer which are fed by a capillary passageway formed in a separate layer. Alternately, the gasket and capillary may be molded as a single piece of material. A wetting agent may be applied to the bottom of the capillary channel to facilitate blood flow without the presence of an absorbent material in which the sample may run. High molecular weight polymeric oils work well as wetting agents. A preferred material is dimethylsiloxane ethylene oxide, part number PS073 from United Chemical Technologies. The same effect may be achieved through the use of patterned hydrophilic printing inks, BSI Corporation Photolink™ hydrophilic surface treatment or using CYREX injection molded part. Thin film materials, used for the front and back layers of the strip, are laminated to either side of the gasket-capillary structure. The wetting agent can be applied to the channel by either an air brush or nylon brush applicator and then dried under a heat lamp. Both methods work equally well.

Separating agents are impregnated into the matrix before, during or after the impregnation of test reagents. The specific compounds are selected to enhance the ability of the matrix to separate whole blood into red blood cells and clear fluid. As discussed previously, the preferred matrix materials comprise a microporous polyethersulfone from Gelman, Pall Hemadyne or Ahlstrom cellulose and glass media.

The separating agents which can be impregnated into the matrix may be selected from the following: polyvinyl sulfonic acid (PVSA), polyethylene glycol (PEG), polystyrene sulfonic acid (PSSA), hydroxypropyl cellulose (commercially available as Klucel™), polyvinyl alcohol (PVA), polyvinylpyrrolidone (PVP), polyacrylic acid (PAA), water soluble salts, citrates, formates and sulfates, amino acids, chitosan (amino sugar), citric acid, phytic acid and malic acid. These materials may be enhanced through combining with silica or clay. The chemical components can include equivalent materials which help to separate whole blood into red blood cells and relatively clear fluid.

Many analytes in blood exist within a narrow range. The largest normal range for any component of whole blood is the fraction of red blood cells in the whole blood, or hematocrit. A healthy individual may have hematocrit ratio between 35 and 55. Persons at high altitudes and newborns often have elevated hematocrit levels, e.g., 60 or above. Sick individuals may experience hematocrit levels of 30 or below. An individual with a hematocrit of 60 has a water soluble analyte, such as glucose, distributed in only 40% by volume of the whole blood sample applied. A 30 hematocrit blood sample is 70% liquid fraction. Those skilled in the art recognize the huge effect this variable composition can have on whole blood test results. (Many hospitals and clinical labs rely on serum analyte levels to eliminate this interference.) The blood separation devices and methods described in the present invention allows for the virtual creation of a serum system by removing the red blood cells from the reaction area. As long as adequate fluid is delivered to the active areas of the device, which the geometries of the device assure, additional clear fluid and red cells held away from the active areas of the device do not impact the reaction. The hematocrit effect, which is a marked influence on the overall performance of most devices, is substantially eliminated in the practice of the present invention.

The indicating reagent mix must be capable of detecting the presence of the analyte. In general, the analyte reacts with a specific oxidase enzyme and produces hydrogen peroxide. This strongly oxidative substance reacts with the indicator(s) present to produce a colored end product. The oxidase enzyme may be one of the following: glucose oxidase, cholesterol oxidase, uricase, alcohol oxidase, aldehyde oxidase or glycerophosphate oxidase. While the examples and preferred embodiments herein comprise glucose oxidase in the formulations, formulation changes required to utilize other oxidase enzymes are evident to one who is skilled in the art. The indicator chemistries which provide acceptable color generation when coated on the microporous membrane (polyethersulfone) from Gelman, Pall Hemadyne or Ahlstrom Filtration glass fiber matrix may be chosen from 3-methyl-2-benzothiazolinone hydrazone hydrachloride (MBTH) combined with 3,3-dimethylaminobenzoic acid (DMAB), MBTH combined with 3,5-dichloro-2-hydroxybenzene-sulfonic acid (DCHBS); 4-aminoantipyrene (4-AAP) (at 4 mg/ml) and 5-Oxo-1-(p-sulfophenyl)-2-pyrazoline-3-carboxylic acid (OPSP); 4-AAP (at 4 mg/ml) and n-(m-tolyl)-diethanolamine (NDA); 2,2'-azino-di (3-ethylbenzthiazoline) sulfonic acid (ABTS); 4 AAP (at 4 mg/ml) and 4-methoxynaphthol; pyrogallol red(PGR); bromopyrogallol red (BPR); acid green 25 (AG); MBTH and 8-anilino-1-naphthalenesulfonate (ANS); or N-(3-sulfopropyl)aniline and MBTH; or other known and conventional dye system for different analytes. U.S. Pat. No. 5,306,623 to Kiser et. al. discloses effective concentrations of a number of useful dye systems.

A preferred dye system is disclosed in copending application Ser. No. 08/628,794, now U.S. Pat. No. 5,776,719 filed on even date herewith and incorporated herein by reference. This preferred dye system is based on the sulfonated form of MBTH, 3-Methyl-6-(M sulfonate)-benzothiazolinone-(2)-hydrazone (MBTH-S) where M is sodium, potassium, ammonium or other equivalent ion, but is preferably sodium. MBTH-S formed as a dye couple with DMAB, ANS or N-(3-sulfopropyl)aniline provides an indicator system which provides a stable color end point in a short period of time. This dye system enables visual reading on a reliable basis without the use of meters or complex timing sequences.

Certain indicators such as MBTH-DMAB continue to change color over time, i.e., the reaction does not reach a stable end point within a reasonable time period. When it is desirable that such an indicator dye system is used, it is important to take the desired readings at specific time after wetting the test strip and beginning the reaction. U.S. Pat. No. 5,049,487 to Phillips et al., incorporated herein by reference, describes the use of a change in reflectance of the matrix as a signal that the matrix has been wetted by the sample. In the present invention, the meter design can incorporate two contacts which make contact with the reagent impregnated test pad. When the test pad has been wetted by the application of blood or test sample, a circuit is made and the timing is initiated. The meter can then take readings at the appropriate times as required by the algorithm in the meter. Alternately, sensors in the meter can detect an object, such as a finger or a pipette, over the test matrix in the area to which sample is applied. The timing can be initiated at the time of or shortly after object detection. Either of these approaches enables the design of a simplified, lower cost meter for use where the indication of the dye system must be measured on a time-dependent basis.

The MBTH-ANS system described by Yu in U.S. Pat. No. 5,453,360 may be used in the methods and devices of this invention. However, both components require an acid pH of approximately 4.0, which enhances enzyme activity and requires the use of higher levels of oxidase or peroxidase enzymes than desired in the chemistry system. A near neutral pH system is more preferred. MBTH-S dye system referred to above can exist at approximately a pH of 6 and has the advantages of being easier to formulate and enhanced enzyme activity. By using MBTH-S and ANS a dye couple can be used which exists at a pH of 6 which permits the dye couple dry chemistry system to be used at this higher pH. It has been found that the MBTH-S and N-(3-sulfopropyl) aniline formulation is another preferred embodiment for the indicating dye system in the devices and methods of this invention. It creates a stable end point chemistry which is water soluble and does not sublime over time when applied and dried in the membrane matrix. The MBTH-S coupled with ANS provides flat spectral absorption in the region of about 580 to 650 nm. MBTH-S coupled with ANS provides good spectral absorption, is water soluble and does not sublime under dry chemistry storage conditions. A preferred dye system of the MBTH-S and ANS dye couple can be used in the device of present invention because of the separation of the red blood cells from the reaction site provided by the devices and methods of present invention. Effective blood separation occurs using the microporous Gelman membrane or lateral wicking Ahlstrom or Pall materials, making spectral absorption in the range of 580–650 nm (see FIG. 27) acceptable. This range produces colors which are purple to blue. The lower end of the wavelength range would not be acceptable for a meter read strip if whole blood color was present in the device test area. The use of tension modifiers, hematocrit adjustment compounds, buffers and chelators which are useful in these systems are known in the art. One who is skilled in the art can formulate an acceptable chemistry based on the components disclosed herein and in the prior art.

The above reagents will create a chemistry which can be read with either by a meter or by visual color comparison. To create a visual strip which can be read in binary fashion as described in U.S. Pat. No. 3,964,871, issued to Hochstrasser, a plurality of test areas must be designed into the test device. To permit the chemistry to be sensitive to threshold levels of analyte an antioxidant is used to inhibit or intercept the reaction in visual test zones which only change color if the analyte is present in greater quantity than the inhibition chemistry in that zone. They participate in a noncompetitive reaction and are consumed first by the hydrogen peroxide. If the antioxidant is fully consumed by the reaction the dye indicator(s) is oxidized and color is developed in the test matrix. Hochstrasser, U.S. Pat. No. 3,964,891, provides the background to the design and implementation of a urine inhibition test strip. Kiser et al, U.S. Pat. No. 5,306,623, expands this for blood testing. Antioxidants which may be utilized include 2,3,4-trihydroxybenzoic acid, propyl gallate, ascorbic acid, isoascorbic acid, 3,4 dihydroxy cinnamic acid, 3,4 dihydroxy benzaldehyde, Gallic acid and 5,6-diaminouracil. The antioxidant which is preferred in this embodiment is ascorbic acid.

The multi-zone test systems can use various indicating reagent technologies:
- indicating dyes and an antioxidant system to provide threshold readings, which can be utilized in multizone nonmetered test formats as described above,
- indicating dyes which are consumed by the reaction, i.e. a test zone with more dye will turn off at higher concentrations of analyte than a test zone with less dye, and
- indicating dyes which are generated in proportion to the concentration of an analyte, which may be used in a color match system or in conjunction with a meter.

A three level sample device can be used in the present invention based on the chemistry systems described below.

| Test Zone | Indicating dye same amount each test area | Indicating Dye + Antioxidant | Indicating Dye + increase concentration for each test area |
|---|---|---|---|
| Low | color match | Dye + minimal antioxidant | Dye |
| Medium | color match | Dye + more antioxidant than the low test zone | Dye + additional dye |
| High | color match | Dye + more antioxidant than the medium test zone | Dye + additional dye + additional dye |

The separation reagents, indicator reagents, oxidase enzymes, peroxidase enzymes, hematocrit adjuster, buffers, antioxidants and chelators together with the dye system are impregnated in a membrane matrix selected from polyethersulfone, polysulfone, polyamide, cellulose and glass fiber or Pall Hemadyne.

The issue of hematocrit level affecting the accuracy of test results is a substantial one for a test device which does not have good blood separation and microtitration. The membranes used in this invention can be used in meter-read devices and, without the microtitration format, may have a larger hematocrit effect than desired. The following embodiment of this invention can be used to compensate for the hematocrit variation of whole blood. The instrument can be designed with additional light sources and receivers (sensors) connected to analog signaling/conditioning circuit. These additional sensors can be implemented so that they inspect a channel in the test device, one sensor at the beginning of the channel and one at the end. Whole blood is applied remote from the reaction zone. The test device has a capillary channel which is clear and the movement of whole blood is timed between sensors. The time that the blood takes to travel up the capillary is an indication of the hematocrit of the blood, and that information is used to correct any shift in reflectance readings of the instrument caused by the hematocrit level. The capillary can have two configurations: a clear channel with a hydrophilic wetting agent applied or a channel formed in a lateral wicking porous material. The layers of preferred embodiments of the invention are fastened with adhesive such as 3 M grade 415 pressure sensitive acrylic adhesive. The porous inert material has a low free radical content and is widely used in medical devices.

The various aspects of the invention disclosed herein can best be illustrated by reference to the drawings and the description thereof which follows.

FIGS. 1 and 2 illustrate a device of this invention which utilizes a porous matrix member 1 to achieve separation of whole blood into red blood cells and relatively clear fluid. Matrix 1 has a skin side 5 and a test side 7 and is attached to holder 49 which contains opening 21. The matrix is preferably an intrinsically hydrophilic material and is optionally impregnated or coated with separating reagents to facilitate and maximize blood separation. A sample of whole blood is applied to the skin side 5 of matrix 1 through opening 21. The combination of the skin characteristics of the matrix, the hydrophilic nature and the separating agents provide blocking of the red cells on the surface of the skin side S while clear fluid containing the analyte flows through the skin into matrix 1 and to test side 7. Indicator reagents are present in the matrix, as well as enzymes, hematocrit adjusters, buffers, antioxidants and chelators, which are useful in providing a test device which is capable of determining the level of an analyte in whole blood. The various indicator reagents are known in the art conventionally formulated into reagent cocktails in solvents and applied to matrix 1. The cocktails for each analyte to be detected are formulated into groups which can coexist in the same pH and solvent solutions conditions. Each indicator or other reagent cocktail is applied to the test side 7 of matrix 1 and dried. When the blood sample wets the reagent present in the matrix, the indicator in the test side of the matrix changes color to provide the desired indication of the analyte, e.g., glucose, in the blood.

As shown in FIG. 3A, a drop of blood or other fluid 30 from the users finger or from an applicator may be applied to the device of FIG. 2 through opening 21 and the color change may be read on test side 7 by a test instrument 72 or by visually color match. FIG. 3A illustrates a typical combination of the device of FIG. 2 as used in conjunction with a test instrument 72. When the test device of FIG. 2 is inserted in the test instrument 72, related and necessary information may be communicated to the test instrument 72 via an instrument readable reference code 61, shown in FIGS. 1 and 2 or by a mechanical notch pattern or a magnetic pattern shown in FIG. 3B at 101. The information contained in the code or pattern provides calibration data, timing sequence or other information to assure accuracy of the reading of the test strip by the instrument. A circuit in test instrument 72 can be completed when the blood or clear fluid from the application of drop 30 wets matrix 1, connecting the contacts 70 and 71 with each other and initiating the test sequence of the instrument or as directed by reference code 61 or pattern 101.

FIGS. 4 and 5 show a device essentially the same as FIGS. 1 and 2 but having multiple reaction zones or areas in matrix 1, multiple blood application apertures 21 in holder 449 and multiple viewing apertures 11 in support member 19. The matrix 1 has a skin side 5 and test side 7 and is impregnated with appropriate indicator reagents. The matrix 1 can be attached with adhesive to holder 449. Holder 449, matrix 1 and support 19 are laminated to form the device shown in FIG. 5. Blood samples are applied to skin side 5 of matrix 1 through apertures 21 in the holder 449 and the color change is observed on the test side 7 of matrix 1 through openings 11 in support member 19. FIG. 39 shows a similar device but with individual, discrete matrix members for each test zone or set of opening. In this embodiment the skin side 5 can include the top and sides of each discrete matrix element to prevent red blood cells from entering a matrix element.

It is to be understood that in all embodiments of this invention where a member is called for as having openings therein for visual reading or meter measurement of the indication of the indicator, it is intended that these are visual or transparent openings. Thus, such a member may be a solid sheet with no physical openings or holes therein, but provides visual or meter access to the indicator by being transparent or sufficiently translucent at least at the appropriate test sites for reading the indicator indications, or may be entirely transparent. Such a member can also be a composite laminate of an opaque layer, such as aluminum foil, with opening therein and a transparent plastic film, with opening therein and a transparent plastic film that is a solid sheet but provides visual access through the openings in the opaque layer.

FIGS. 6 and 7 show a device essentially the same as FIGS. 4 and 5 but having a blood delivery system for distributing a blood sample internally in the device. The blood delivery system is comprised of gasket layer 13 containing openings 621, laminated to a channel layer 23 containing capillary passageway 25 communicating with notches 33 which form reservoirs above openings 621. Blood is applied to the device through sample receiving opening 29 in cover member 31. The blood travels through the capillary passageway 25 which flow may be assisted by a wetting agent applied to the bottom thereof. The capillary passageway 25 is vented by cut outs 24 in the channel layer 23, which communicates with vent 22 in gasket layer 13. Blood fills the notches 33 forming reservoirs in the channel layer 23 and passes through openings 621 to the skin side 5 of matrix 1. Channel layer 23 and gasket layer 13 can be coated with a wetting agent to aid in blood flow through the channel or can be an inherently hydrophilic plastic, such as a sulfonated plastic. The blood is separated into relatively clear fluid which is passed through skin side 5 to test side 7 of matrix 1 and red blood cells which are retained on the surface of skin side 5. The color formed in the indicator in the test side 7 of matrix 1 is viewed through openings 11 in support member 19. The device of FIGS. 6 and 7 is made by laminating cover member 31, channel layer 23, gasket layer 13, matrix 1 and support 19 to form a unitary device. Appropriate adhesives may be used between the various layers to provide adhesion of the layers into the formation of the unitary device of FIG. 7 and to provide appropriate sealing of the multiple test zones from each other and to provide a confined internal path for the blood sample to flow from opening 29 through the confined path defined the capillary passageway 25, notches 33, openings 621 to the skin side 5 of matrix 1 and prevent any flow of fluid from one test zone to another. In this manner each individual test area defined by openings 11 and support member 19 can be observed according to the indicator present in the corresponding zone of the test side 7 of matrix 1. It may be desirable to have different indicator reagents present in each different test zone. Alternatively it may be desirable to have a graduated concentration of indicator reagent different indicator reagents along the length of matrix 1 whereby the color change in openings 11 will be graduated for a given blood sample to provide the desired reading or measurement from the indicator or indicators present.

FIGS. 8A, 8 B and 9 illustrate the devices constituting another aspect of the present invention. In this aspect a substantially noncompressible member 93 is provided with opening 91 having a predetermined volumetric size. A matrix member 1 having a skin side 5 and test side 7 as shown in FIG. 1 is compressed against member 93 such that a portion of matrix 1 protrudes or extends into opening 91 and the remaining portion of matrix 1 is compressed to a thinner layer as illustrated in FIG. 8B. For illustration purposes FIG. 8B shows partially compressed matrix member 1 separated from member 93. However, it is understood once matrix member 1 is compressed against member 93 and into opening 91 it need not be separated from member 93 but may be positioned directly on holder 9 to result in the unitary device illustrated in FIG. 9. In this device the skin side of matrix 1 which protrudes into opening 91 of member 93 remains exposed for application of a blood sample in opening 91 with the test side of matrix 1 being visible for reading or measurement through opening 96 and holder 9. It is further to be understood that the orientation of matrix 1 may be reversed in this device whereby the test side 7 of matrix 1 is compressed against member 93 and protrudes into opening 91 leaving the skin side of matrix 1 to contact holder 9. In such reverse configuration the blood sample can be applied through opening 96 to the skin side 5 of matrix 1 then the reading or measurement of sample side 7 of matrix 1 can be performed through opening 91. As illustrated in FIGS. 1, 2 and 3, the device of FIGS. 8A, 8 B and 9 can contain machine readable coding 62 for calibration or control of a test instrument as indicated above.

Another embodiment of this aspect of the invention is illustrated in FIG. 8A, after matrix member 1 is compressed against member 93 to form the protrusion of matrix member 1 into opening 91 the partially compressed matrix 1 can be removed from member 93 and placed on holder 9 as shown in FIG. 8A. In this embodiment the protruding noncompressed portion of partially compressed matrix 1 is inserted into opening 96 to provide a simple device on which a blood sample may be applied to opening 96 and skin side 5 of matrix 1 and the indicator read or measured on test side 7 of matrix 1. It will further be apparent and understood that in making the device of FIG. 9 matrix 1 can be compressed between member 93 and holder 9 in an appropriate lamination process with appropriate adhesives. In such a process opening 96 is temporarily blocked with a tool to prevent matrix 1 from protruding into opening 96 during the lamination and compression.

An important aspect of the device shown in FIG. 8B and 9 is that opening 91 is provided to have a predetermined volumetric size. This volumetric opening is substantially filled with the protruding portion of matrix 1 containing an indicator reagent. This configuration thereby provides a specific known and predetermined volume in opening 91 which provides a microtitration chamber of a given volume for a given quantity of indicator in the protruding matrix 1 positioned within volumetric opening 91. Thus, in addition to an ordinary color indication by an indicator, this device can provide a specific, concentration indication on a titration basis for a known volume of fluid filling volumetric opening 91 and a given amount or concentration of indicator or other reagent present in volumetric opening 91.

As described above a blood sample applied to the device of FIG. 9 or the device of FIG. 8A is applied to the skin side of matrix 1 present in volumetric opening 91 or volumetric opening 96, whereby the red blood cells or other solids are blocked from passage by skin side 5 and the blood fluids are passed through skin side 5 to test side 7 of matrix 1.

FIGS. 10A and 10B show a device essentially the same as FIGS. 8B and 9 but having multiple volumetric openings 91 with multiple portions of matrix 1 protruding therein. The construction and use of the devices of FIGS. 10A and 11 are the same as for the devices of FIGS. 8B and 9 except that multiple test zones are provided. FIG. 11 is a illustration of an alternative configuration showing that the portions of matrix 1 which protrude into volumetric openings 91 may be rounded in nature as opposed to exactly conforming to the full volume of volumetric opening 91. It is not necessary for the portion of matrix 1 protruding into volumetric opening 91 to completely fill the available volume of volumetric opening 91. It is simply necessary that the amount or portion of matrix 1 which does protrude into volumetric opening 91 when compressed against member 93 be known and calibrated in order that accurate volumetric titration tests can be performed for the given volume of volumetric opening 91 and a given amount of indicator or reagent present in the matrix protruding into volumetric opening 91. In use the volumetric opening 91 can be filled with a given and known volume of test fluid whether or not the volumetric opening 91 is completely filled with the protruding portion of matrix 1.

The device of FIGS. 12 and 13 are essentially the same as the devices of FIGS. 10A and 10B but with the added feature of an internal capillary passageway for distributing a blood sample internally to the various test zones, as described above in connection with the device shown in FIGS. 6 and 7. In use the sample enters opening 29, flows through capillary passageway 25 to notches 33 and openings 621 to the skin side 5 of matrix 1. The fluid portion passes through skin side 5 to test side 7 and the indicator, which is read or measured through openings 11.

FIGS. 14, 15 and 16 illustrate a modification of the device of FIGS. 12 and 13 wherein the layout of the test sites are configured such that the flow of blood through capillary 25 can be aided by gravity flow. In this device the blood sample is introduced through opening 29 in cover member 31. The blood can flow through capillary passageway 25 and openings 33 to contact the skin side 5 of the protrusions of matrix 1 positioned in opening in member 35. When the assembled device of FIG. 14 is placed on its edge with opening 29 at the top edge it can be seen that gravity will assist in the flow of the blood along capillary passageway 25 and through notches 33 and vents 36. FIG. 16 shows support member 19 having a corresponding arrangement of openings 11 to correspond to the layout of the protrusions of the matrix member 1. FIGS. 37 and 38 show the same device with user instructions on one side, i.e., where to apply the blood sample, and indicia on the other side for visual indication of the test results, i.e., level of glucose concentration.

FIGS. 17, 18, 19 and 20 illustrate a variation of the device of FIGS. 12 and 13. In this configuration matrix 1 is compressed against member 34 as shown in FIG. 17, which results, after removal of the compressed matrix 1 from member 35 in a partially compressed matrix 1 having a protrusion of uncompressed portion of matrix 1 as shown in FIG. 18. FIG. 19 illustrates the remaining uncompressed portion of matrix 1 after most of the compressed portion of matrix 1 has been removed from around the uncompressed portion leaving element 17 which is a uncompressed shape of matrix 1 having a small border around the base thereof of compressed matrix 1. These elements may then be assembled into appropriate openings such as the volumetric openings 91 illustrated in FIG. 10A. As shown in FIG. 20 the matrix elements 17 may be assembled so that they fit into openings in member 35 and sealed by adhesive around the border at the base of each matrix element. This type of device can be assembled and used as described above with respect to the devices of FIGS. 12, 13 and 14.

FIGS. 21 and 22 illustrate another aspect of the present invention wherein the porous matrix is utilized in a device having an offset configuration. This device provides for the lateral transfer of the fluid sample through the matrix member to provide certain advantages in the reading or measurement of the indicators. As shown in FIG. 21 holder 49 contains opening 21, matrix 40 is positioned between holder 49 and support 19, and support 19 contains opening 11 which is laterally offset a given distance from opening 21 in holder 49. In this device matrix 40 has initial area 47 corresponding to opening 21 and test area 45 corresponding to opening 11. A sample fluid is introduced through opening 21 into initial area 47 of matrix 40, passes laterally through matrix 40 into test area 45 and reacts with the indicator, which can be read or measured through opening 11. Matrix 40 is a porous matrix containing pores capable of blocking in the lateral distance between the initial area 47 of matrix 40 and test area 45 the passage of solids but is capable of allowing the passage of fluid from initial area 47 to test area 45. In this device the matrix material 40 provides a separation of the solids such as red blood cells over the lateral distance from initial area 47 to test are 45 such that the indicator present in test area 45 as viewed through opening 11 will be substantially free from solids or red blood cells which may interfere with the indication provided by the indicator reagents in the test area 45 of matrix 40.

FIGS. 23 and 24 illustrate a device similar to FIGS. 21 and 22 wherein matrix member 40 is compressed against member 93 whereby a portion of matrix member 40 is compressed against the surface of 93 and a portion of matrix member 40 protrudes into opening 91 of member 93. This configuration is similar to that described above with respect to FIG. 8B and 9, except in this configuration the opening 91 is elongated thus providing an elongated protrusion of uncompressed portion of matrix 40 in order to provide an uncompressed portion of matrix 40 extending from opening 21 in holder 49 to the offset location of opening 11 in support member 19. Thus FIG. 24 shows the assembled device with member 93 and matrix 40 positioned between holder 49 and support member 19. In this device a fluid sample in introduced in opening 21 where it passes through initial area 47 of matrix 40 and flows laterally through matrix 40 to test area 45 which is positioned to correspond with opening 11. As described above in the lateral distance between initial area 47 and test area 45 the porous nature of matrix 40 is capable of blocking the passage of solids, such as red blood cells, and allowing passage of fluid to test area 45 to react with indicator present in test area 45, which indication can then be viewed through opening 11.

The device of FIGS. 25 and 26 is essentially the same as the device illustrated and described in FIGS. 21 and 22 but having multiple reaction zones. Otherwise the configuration is similar in that openings 21 correspond to initial area 47 and openings 11 correspond to test area 45 of matrix 40. The function of the device of FIGS. 25 and 26 is the same as the device FIGS. 21 and 22 but on a multiple zone basis.

The device of FIG. 27 is essentially the same as the device illustrated and described in FIGS. 23 and 24 except in a multiple test zone configuration. Similarly the device of FIGS. 28 and 29 correspond to the device of FIGS. 25 and 26 but further incorporating the internal capillary passageway distribution system for the fluid as described above in connection with FIGS. 6 and 7. Similarly, FIG. 30 illustrates a device of FIG. 27 but with internal capillary passageway distribution system for the fluid.

FIGS. 31 and 32 illustrate another aspect of the devices of the present invention which enable analysis of an analyte in a fluid by measuring the initial flow rate through a restricted flow passageway. In this device member 323 contains first opening 322 and second opening 366 with restricted flow passageway 325 communicating with the first opening and the second opening, whereby the fluid sample introduced into the first opening 322 will flow by capillary action through passageway 325 to opening 366. The device further comprises cover layer 331 having opening 321 corresponding to opening 322. The device further comprises transparent support member 319 having opening 311 corresponding to opening 366, which can optionally have matrix member 1 compressed into or preshaped to fit into opening 366. In this device support member 319 is transparent so that the flow of fluid from opening 322 through passageway 325 to opening 366 can be observed and can be measured by detector 64. Detector 64 is adapted to measure the rate at which the initial flow of fluid occurs from opening 322 through passageway 325. The rate of flow of the fluid can be correlated to known concentrations of an analyte in the fluid so that measuring the rate of initial flow of a know fluid for a known analyte will provide the concentration of the analyte in the fluid being tested. When the fluid reaches opening 366 and flows into matrix 1 containing appropriate indicator reagents, the typical reaction will occur and the indication of the indicator can be observed or measured through opening 311 and support member 319. This configuration presents several distinct advantages. The sample may be applied to the test strip away from the reading area, which may limit biohazard exposure if the meter is used with multiple patients. The rate of travel through the capillary corresponds to the hematocrit of the blood sample. By calculating the lag as the blood moves from one point in the channel to another, a hematocrit may be determined. If appropriate, a hematocrit correction factor may be applied to the test result, improving overall system performance.

FIG. 33 is an illustration of a device which is a variation of the device illustrated and described in FIGS. 31 and 32. In this device passageway 325 contains a portion of matrix 1 which is portion 67 corresponding to the shape of passageway 325. In this configuration of the device the flow rate of fluid from opening 322 to opening 366 will be observed and measured through transparent member 319 as it flows through matrix 67 to opening 366. As with the device in FIGS. 31 and 32 the initial flow rate of a particular fluid through passageway 325 containing matrix 67 can be correlated to the flow of fluid through the identical device for known concentration of the analyte of interest.

FIGS. 34, 35 and 36 illustrate a device similar to the devices shown and described in FIGS. 10A and 20, wherein. The passageway for internal distribution of the fluid is contained on the bottom side of cover member 31 wherein channel 340 communicates with opening 29 and with openings 91 and member 93. In this device fluid sample enters opening 29 in cover member 31 and flows laterally through channel 340 (shown in bottom view of cover member 31 in FIG. 36) to each of the opening 91 and member 93 where the fluid contacts each of matrix elements 37. The fluid flows through skin side 5 and into matrix elements 37 containing the indicator reagent. Thus the indication of the indicator can be viewed measured through openings 11 in support member 19.

In general the matrix material 1 such as illustrated in FIGS. 1 and 2 will generally by in the ranges of about 3 mils to 7 mils in thickness. (1 mil=0.001 inch=0.0254 mm.) In most test devices a thickness of about 4 to 5 mils is preferred. On the skin side 5 of matrix 1, the thickness of the skin capable of blocking the passage of red blood cells will be about 0.5 mil or less. The holder member such as 49 in FIGS. 1 and 2 will generally be a polymeric strip having a thickness from about 5 mils to about 12 mils in most applications and depending on the type of polymeric strip employed a thickness of about 7 to 8 mils is preferred for the holder member. The support member such as 19 in FIG. 4 can also have a thickness of from about 5 mils to about 12 mils with about 7 to 8 mils in thickness being preferred when the support member is polymeric. The support member may also be made of a metal foil such as aluminum foil in which case the support member may have a thickness of about 1 to 3 mils in thickness. It will be apparent that when the support member is a metal foil it may be laminated with a transparent plastic film where the openings in the metal foil are appropriately positioned and the transparent film is laminated between the foil and the matrix member where the transparent polymeric film can provide protection of the matrix member containing the indicator reagent from contamination. It will further be recognized that a support member can also be a transparent polymeric strip where the openings are merely visually transparent areas which allow reading or measurement of the indication of the indicator on the matrix member.

Certain member of the devices of this invention such as 93, 13 and 35 which provide fixed volumetric openings into which the matrix material is compressed will generally be in the range of 4 to 12 mils in thickness and preferably about 4 to 5 mils in thickness. It will also be recognized that these members providing the volumetric fixed size openings will preferably be injection molder materials but can be sufficiently rigid in noncompressible polymeric strips from which the desired volumetric opening has been punched or dye cut.

It will be recognized by those skilled in the art that the overall thickness of the assembled test strip devices according to this invention may vary according to the desired use. The overall thickness of the assembled devices can range from about 8 to about 40 mils. Due to the strength provided by laminating the various layers thinner layered materials may be used and provide sufficient strength. However, the overall thickness of a test strip device according to this invention will be determined also by the necessary and desired thickness of the matrix member to provide color separation and sufficient volume absorption. In addition the embodiments of this invention providing the fixed volumetric openings will dictate the thickness of the layers providing the volumetric openings of desired volume for the titration tests enabled by the devices of this invention.

When the matrix member is compressed into the adjacent member as in FIGS. 8A, 8 B and 9, the typical matrix material having a thickness of about 5 to about 12 mils will be compressed in the compressed area to a thickness of about 1 mil or less and typically less than about 0.5 mil At the same time the portion of the matrix layer which protrudes into the volumetric opening will remain at or near its full original thickness.

In the embodiments of the devices according to FIGS. 31 and 33, the restricted flow capillary passageway will typically be about 5 to 25 mils in length. The length of the passageway will be determined by the optical detectors used to detect and measure the initial flow rate of fluid through the passageway and will be determined by the nature of the flow rate and flow pattern of the fluid being detected in the passageway. Typically a passageway of 5 to 10 mils in length is sufficient to measure the initial flow rate of the fluid through the passageway. It has been found that for a plastic channel treated with a dimethyl siloxane ethylene oxide wetting agent the cross section should be about 5 mils by about 40 mils but can be as small as about 5 mils by about 25 mils. Similar size channel is useful in a plastic member without a wetting agent provided the plastic inherently hydrophilic.

The methods of assembling the devices according to the present invention will be apparent to one skilled in the art following the teaching contained herein together with conventional laminating techniques for application of adhesive to the various layers, heat bonding various layers and similar techniques for assembly of the devices disclosed herein.

The devices of this invention are conveniently made into test strips of convenient size and configuration particularly for individual use by visual inspection or for use in instruments or meters which are adapted to measure the color or other indication provided by the test strips. It is also convenient to provide the test strip devices of the present invention in a kit form for use by an individual wherein the kit contains a test strip according to the present invention, an antiseptic applicator, an anesthetic applicator, a sharp article for puncturing the skin or the individual to provide a blood sample, and a bandage for the skin puncture site. When supplied in this kit form, proper and consistent use by the individual will be encouraged and facilitated due to the convenience of the kit.

It is desirable to have a system, or kit, which contains all the necessary supplies for performing a test. This is particularly advantageous for diabetics, many of whom are highly mobile. This invention describes a visual test strip which lends itself well to incorporation in a kit. An individually foil wrapped strip coupled with a commercially available disposable lancing device provides the minimum supplies required to perform a blood glucose test. The kit may optionally include a prepackaged towlette to clean and/or numb the test area and an adhesive bandage to cover the lanced site. The presentation of a complete testing kit is extremely useful for individuals as well as for clinics or visiting nurse groups where complete segregation of all testing supplies from patient to patient is advantageous.

One example of a material useful for lateral transfer of fluid containing analyte and blocking lateral transfer of solids is a composite cellulose and glass fiber matrix, such as that available from Ahlstrom as part number 1661 or 1662, especially to separate the whole blood into red blood cells and substantially clear fluid. Another example is Pall Hemadyne membrane. The whole blood is applied to the matrix and wicks laterally into the matrix material. As the sample wicks, the red blood cells adhere to the glass fibers or other matrix fibers and the clear fluid moves laterally into the test area where the dry reagents are present. The reagents in the test area of the matrix are rehydrated by the clear fluid component of the whole blood and are then able to indicate the presence and concentration of one or more analytes of interest. Separating agents impregnated into the matrix can assist with the separation of red blood cells and facilitate the wicking of the substantially clear fluid into the test area. This configuration coupled with microtitration devices and methods described above will produce an accurate test device.

The following is an example of making and using the devices of this invention.

EXAMPLES

Glucose Test

| Example A: Test Reagents | |
| --- | --- |
| Reagent 1a | 40 mg MBTH-S |
| | 80 mg DMAB |
| | 5 ml acetonitrile and 5 ml water |
| | Stir until all solids are dissolved. |
| Reagent 2a | 6 ml water |
| | 10 mg EDTA, disodium salt |
| | 200 mg PolyPep, low viscosity (Sigma) |
| | 0.668 g sodium citrate |
| | 0.523 g citric acid as a hematocrit adjuster |
| | 0.2 M Aconitic acid buffer |
| | 3% polyethylene glycol (PEG), as a separating agent |
| | 0.5% Polyquart, a binder |
| | 2.0 ml 6 wt % Gantrez AN-139 dissolved in water (GAF) |
| | 30 mg horseradish peroxidase, 100 units/mg, and 3.0 glucose oxidase, 200 units/ml |
| | Stir until dissolved. |
| Reagent 3a | Antioxidant solution of 50:50 ethanol and ascorbic acid at a pH of 4.0, in varying amounts. |

| Example B: Test Reagents | |
| --- | --- |
| Reagent 1b | 20 ml water |
| | 420 mg citric acid (a buffering agent). Adjust th pH of the citric acid solution with NaOH to a value of 4.25. |
| | 16.7 mg EDTA |
| | 90 mg Gantrez S95 available from GAF |
| | 250 mg Crotein SPA |
| | 20,500 units glucose oxidase |
| | 16,200 units peroxidase |
| Reagent 2b | 10 ml of a mixture of 3 parts by volume water and 7 parts by volume isopropyl alcohol |
| | 13 mg MBTH-S |
| | 40 mg ANS |
| Reagent 3b | Antioxidant solution of ethanol and ascorbic acid in varying amounts. |

Test A
Polyethersulfone matrix

A piece of polyethersulfone membrane is uniformly coated with reagent 1a; the excess is squeegied off and the material is dried. The membrane is then coated with reagent 2a in the same fashion and dried. The antioxidant solution reagent 3a is directly applied to the test areas in varying concentrations using a syringe. The membrane is then assembled into a test device as shown in FIG. 2. Whole blood is applied to the sample opening and the glucose level is read from the front based on the indicator response in each of the test zones.

Cellulose and Glass Fiber

A piece of cellulose and glass fiber matrix is discretely coated with reagent 1a and dried. It is then discretely coated with reagent 2a and dried. The antioxidant solution reagent 3a is applied to each test area in varying concentrations using a syringe. The membrane is then assembled into a test device as shown in FIG. 21. Whole blood is applied to the sample opening and the glucose level is read from the opening on the opposite side.

Pall Hemadyne Membrane

A piece of Pall Hemadyne membrane is uniformly coated with reagent 1a, excess fluid is squeegied off and the material is dried. It is then uniformly coated with reagent 2a in similar fashion and dried. The antioxidant solution reagent 3a is applied discretely to each test area in varying concentrations using a syringe. Whole blood is applied to the sample opening and the glucose level is read from the front.

Test B
Polyethersulfone matrix

A piece of polyethersulfone membrane is uniformly coated with reagent 1b, the excess is squeegied off and the material is dried. It is then coated with reagent 2b in the same fashion and dried. The antioxidant solution reagent 3b is applied to the test areas in varying concentrations using a syringe. The membrane is then assembled into a test device as shown in FIG. 2. Whole blood is applied to the sample opening and the glucose level is read from the front based on the indicator response.

Cellulose and Glass Fiber

A piece of cellulose and glass fiber matrix is discretely coated with reagent 1b and dried. It is then discretely coated with reagent 2b and dried. The antioxidant solution reagent 3b is applied to each test area in varying concentrations using a syringe. The membrane is then assembled into a test device as shown in FIG. 21. Whole blood is applied to the sample opening and the glucose level is read from the front.

Pall Hemadyne Membrane

A piece of Pall Hemadyne membrane is uniformly coated with reagent 1b, excess fluid is squeegied off and the material is dried. It is then uniformly coated with reagent 2b in similar fashion and dried. The antioxidant solution reagent 3b is applied discretely to each test area in varying concentrations using a syringe. Whole blood is applied to the sample hole and the glucose level is read from the front.

The dry chemistry reagent system can be used with the identified membranes in many different ways. The system can be used to develop a visual strip for multiple analytes or for varying concentrations of the same analyte. The system can be used for meter read or color match tests. Additional enhancements can be developed by interfacing the strips with a meter and providing novel interface systems for the test device and meter. The following systems could be incorporated into a test device to provide calibration information and start of test signals:

Barcode on strip

Magnetic strip

Notches or magnetic printed areas in the handle of the strip which interface with contacts or reed switches in the meter to provide a binary value, i.e. a 1 equals present and a 0 equals not present. Thus, 16 different settings can be coded into the strip as follows.

| Value | Notch A | Notch B | Notch C | Notch D |
| --- | --- | --- | --- | --- |
| 0 | 0 | 0 | 0 | 0 |
| 1 | 1 | 0 | 0 | 0 |
| 2 | 0 | 1 | 0 | 0 |
| 3 | 1 | 1 | 0 | 0 |
| 4 | 0 | 0 | 1 | 0 |
| 5 | 1 | 0 | 1 | 0 |
| 6 | 0 | 1 | 1 | 0 |
| 7 | 1 | 1 | 1 | 0 |
| 8 | 0 | 0 | 0 | 1 |
| 9 | 1 | 0 | 0 | 1 |
| 10 | 0 | 1 | 0 | 1 |
| 11 | 1 | 1 | 0 | 1 |

-continued

| Value | Notch A | Notch B | Notch C | Notch D |
|-------|---------|---------|---------|---------|
| 12 | 0 | 0 | 1 | 1 |
| 13 | 1 | 0 | 1 | 1 |
| 14 | 0 | 1 | 1 | 1 |
| 15 | 1 | 1 | 1 | 1 |

We claim:

1. A method for determining a corrected concentration of an analyte present in a fluid comprising:
    providing a device comprising:
        a member comprising a first opening for receiving a fluid sample and a second opening for receiving fluid from the first opening;
        a restricted passageway communicating with the first opening and the second opening whereby the fluid sample flows from the first opening to the second opening;
        a detector for measuring a rate of flow of the fluid sample through the restricted passageway; and
        a porous matrix positioned in the second opening which comprises an indicator regent for measuring the concentration of the analyte in the fluid sample;
    applying the fluid to the first opening;
    measuring the rate of flow of the fluid through the passageway;
    measuring the analyte concentration from the indicator reagent;
    correlating said rate of flow to known hematocrit values;
    calculating a hematocrit correction factor from the correlation; and
    applying the hematocrit correction factor to the measured analyte concentration in the fluid to obtain a corrected concentration of the analyte.

2. A method according to claim 1 wherein the porous matrix comprises a polyethersulfone membrane.

3. A method according to claim 1 wherein the porous matrix comprises a cellulose and fiber glass matrix.

4. A method according to claim 1 Wherein the porous matrix and indicator regent is positioned in said second opening having a predetermined volume.

5. A method according to claim 2 wherein the porous matrix and indicator reagent is positioned in said second opening having a predetermined volume.

6. A method according to claim 3 wherein the porous matrix and indicator reagent is positioned in said second opening having a predetermined volume.

* * * * *